US010393754B2

(12) United States Patent
Zhang et al.

(10) Patent No.: US 10,393,754 B2
(45) Date of Patent: Aug. 27, 2019

(54) METHODS OF DIAGNOSING AND TREATING HEART FAILURE

(75) Inventors: Pingbo Zhang, Ellicott City, MD (US); Jennifer E. Van Eyk, Baltimore, MD (US); Anne M. Murphy, Towson, MD (US); Ger Stienen, Abcoude (NL); Jolanda van der Velden, Amsterdam (NL); Viola Kooij, Alphen (NL)

(73) Assignees: CEDARS-SINAI MEDICAL CENTER, Los Angeles, CA (US); VU-VUMC IP MANAGEMENT BV, Amsterdam (NL)

( * ) Notice: Subject to any disclaimer, the term of this patent is extended or adjusted under 35 U.S.C. 154(b) by 1264 days.

(21) Appl. No.: 13/579,797

(22) PCT Filed: Feb. 17, 2011

(86) PCT No.: PCT/US2011/025301
§ 371 (c)(1),
(2), (4) Date: Jan. 15, 2013

(87) PCT Pub. No.: WO2011/103330
PCT Pub. Date: Aug. 25, 2011

(65) Prior Publication Data
US 2013/0101606 A1 Apr. 25, 2013

Related U.S. Application Data

(60) Provisional application No. 61/305,298, filed on Feb. 17, 2010.

(51) Int. Cl.
G01N 33/68 (2006.01)
C07K 16/18 (2006.01)
B82Y 15/00 (2011.01)

(52) U.S. Cl.
CPC ......... *G01N 33/6887* (2013.01); *C07K 16/18* (2013.01); *B82Y 15/00* (2013.01); *C07K 2317/34* (2013.01); *G01N 2800/325* (2013.01); *Y10S 977/774* (2013.01)

(58) Field of Classification Search
None
See application file for complete search history.

(56) References Cited

U.S. PATENT DOCUMENTS

2004/0072255 A1 4/2004 Van Eyk et al.
2009/0181405 A1 7/2009 Jin

FOREIGN PATENT DOCUMENTS

EP 3178846 A2 6/2017
EP 3178846 B1 8/2018
WO 2011103330 A2 8/2011

OTHER PUBLICATIONS

Clinical Chemistry 2003, 49(6):873-879.*
Layland, J., et al., "Regulation of cardiac contractile function by troponin I phosphorylation" Cardiovasc Res. 2005; 66:12-21.
Yuan, C., et al., "Discovery of disease-induced post-translational modifications in cardiac contractile proteins" Curr Opin Mol Ther. 2005; 7:234-239.
Jaquet, K., et al., "Characterization of the cardiac troponin I phosphorylation domain by 31P nuclear magnetic resonance spectroscopy" Biochemistry 1993; 32:13873-13878.
Beier, N., et al., "Isolation and characterization of a highly phosphorylated troponin from bovine heart" Eur J Biochem. 1988; 176:327-334.
Kobayashi, T., et al., "A non-equilibrium isoelectric focusing method to determine states of phosphorylation of cardiac troponin 1: identification of Ser-23 and Ser-24 as significant sites of phosphorylation by protein kinase C" J Mol Cell Cardiol. 2005; 38:213-218.
Messer, A., et al., "Troponin phosphorylation and regulatory function in human heart muscle: Dephosphorylation of Ser23/24 on troponin I could account for the contractile defect in end-stage heart failure" J Mol Cell Cardiol. 2007; 42:247-259.
Zaremba, R., et al., "Quantitative analysis of myofilament protein phosphorylation in small cardiac biopsies" Proteom Clin Appl. 2007; 1:1285-1290.
Gallon, C., et al., "Cellular dysfunction and altered contractile protein post-translational modification in hypertrophtc cardiomyopathy" J Mol Cell Cardiol. 2008; 44:746-752.
Messer, A., et al., "Analysts of cardiac myofibrillar troponin I phosphorylatton in normal and failing human hearts using phos-tags" Biophys J. 2009; 96:501a-501a.
Bodor, G., et al., "Troponin I phosphorylation m the normal and failing adult human heart" Circulation 1997; 96:1495-1500.
Zakhary, D., et al., "Protein kinase A (PKA)-dependent troponin-I phosphorylation and PKA regulatory subunits are decreased in human dilated cardiomyopathy" Circulation 1999; 99:505-510.
Van Der Velden, J., et al., "Increased Ca2+ sensitivity of the contractile apparatus m end-stage human heart failure results from altered phosphorylation of contractile proteins" Cardiovasc Res. 2003; 57:37-47.
Murphy, A. "Heart failure, myocardial stunning, and troponin: a key regulator of the cardiac myofilament" Congest. Heart Fail. 2006; 12: 32-38.
Bilchick, K., et al., "Heart failure-associated alterations in troponin I phosphorylation impair ventricular relaxation afterload and force-frequency responses and systolic function" Am J Physiol Heart Circ Physiol. 2007; 292: H318-H325.

(Continued)

*Primary Examiner* — Sharon X Wen
(74) *Attorney, Agent, or Firm* — Seth D. Levy; Nixon Peabody LLP

(57) ABSTRACT

This invention relates to novel phosphorylation sites in cardiac Troponin I that are associated with the onset of heart failure. The phosphorylation sites, i.e., serine 5, tyrosine 26, threonine 51, serine 166, threonine 181 and/or serine 199, can be used as biomarkers for (i) identifying subjects at risk for the development of heart failure, (ii) treating subjects having a higher than normal level of the biomarker, and (iii) monitoring therapy of a subject at risk for the development of heart failure. Also described are antibodies, reagents, and kits for carrying out a method of the present invention.

11 Claims, 14 Drawing Sheets

(56) References Cited

OTHER PUBLICATIONS

Tachampa, K., et al., "Cardiac troponin I threonine 144: role in myofilament length dependent activation" Circ Res. 2007; 101 1081-1083.

Takimoto, E., et al., "Frequency- and afterload dependent cardiac modulation in vivo by troponin I with constitutively active protein kinase A phosphorylation sites" Circ Res 2004; 94: 496-504.

Pi, Y., et al., "Phosphorylation oftroponin I controls cardiac twitch dynamics. Evidence from phosphorylation site mutants expressed on a troponin-I null background" Circ Res. 2002; 90:649-645.

Layland, J., et al., "Essential role of troponin I in the positive inotropic response to isoprenaline in mouse hearts contracting auxotonically" J Physiol2004;556:835-47.

You, B., et al., "Phosphorylation of cardiac troponin I by mammalian sterile 20-like kinase 1" Biochem J. 2009; 418:93-101.

Kooij, V., et al., "Protein kinase C alpha and epsilon phosphorylation oftroponin and myosin binding protein C reduce Ca(2+) sensitivity in human myocardium" Basic Res Cardiol. 2010; 105:289-300.

Van Eyk, J., et al., "The biological importance of each amino acid residue of the troponin I inhibitory sequence 104-115 in the interaction with troponin C and tropomyosin-actin" J Biol Chem. 1988; 263:1726-1732.

Messer, A., et al., The use of phosphate-affinity SDS-PAGE to measure the cardiac troponin I . . . , Proteomics Clinical Applications, Oct. 13, 2009, vol. 3, pp. 1371-1382.

Bar-Or, D., et al., "Diagnostic potential of phosphorylated cardiac troponin I as a sensitive . . . ", Clinica Chimica Acta, Jun. 21, 2005, vol. 362, pp. 65-70.

Katrukha, A., et al., "Troponin I is released in bloodstream of patients with acute myocardial . . . ", Clinical Chemistry, Aug. 1997, vol. 43, No. 8, pp. 1379-1385.

Haworth, R., et al., "Protein kinase D is a novel mediator of cardiac troponin I . . . ", Circulation Research, Oct. 28, 2004, vol. 95, pp. 1091-1099.

PCT/US2011/025301 International Search Report and Written Opinion dated Feb. 21, 2012; 12 pages.

PCT/US2011/025301 International Preliminary Report on Patentability dated Aug. 21, 2012; 7 pages.

Extended Search Report for EP 11745251.6 dated Sep. 16, 2013, 7 pages.

Partial Search Report for EP 17152485.3 dated Mar. 20, 2017, 8 pages.

Extended Search Report for EP 17152485.3 dated Jun. 27, 2017, 8 pages.

\* cited by examiner

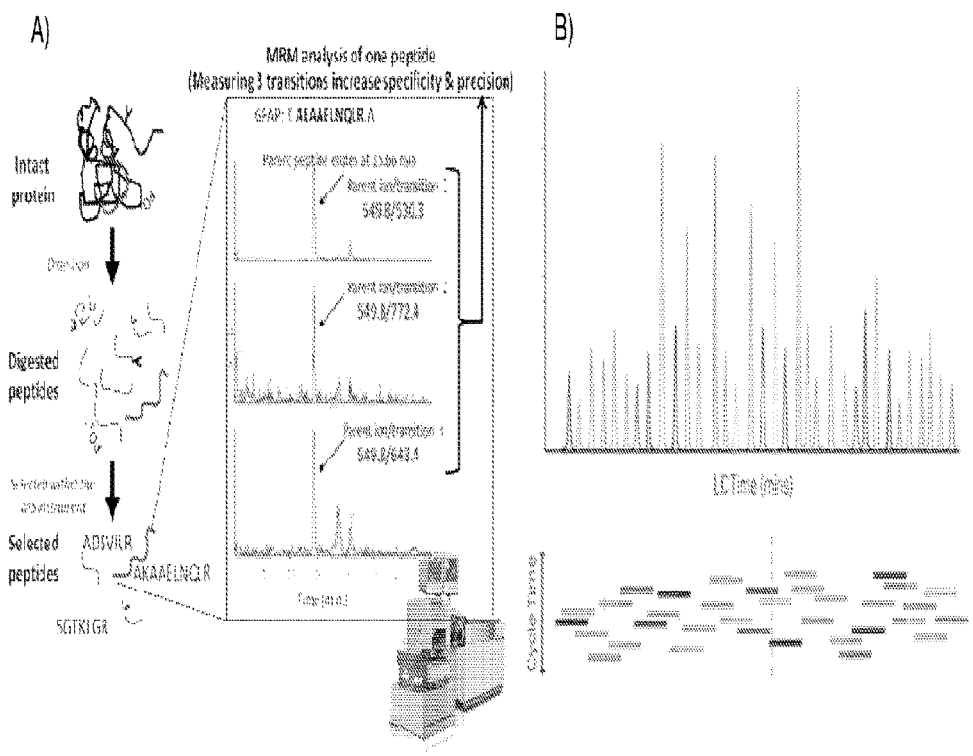
Figure 1. An illustration of MRM assay A) MRM measures peptides unique to a target protein; B) Scheduled MRM™ Algorithm.

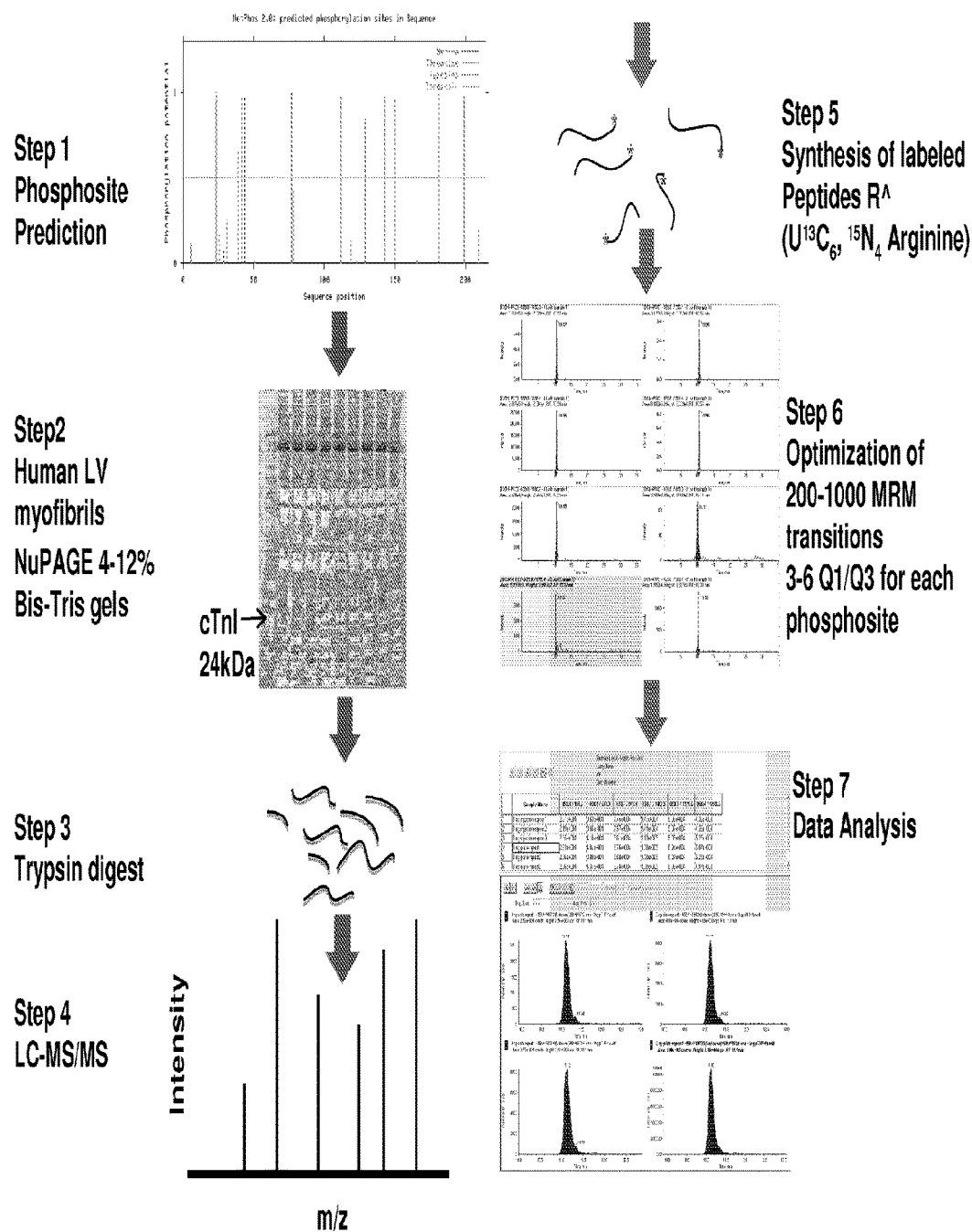
Figure 2 Schematic MRM phosphorylation assay for cardiac troponin I.

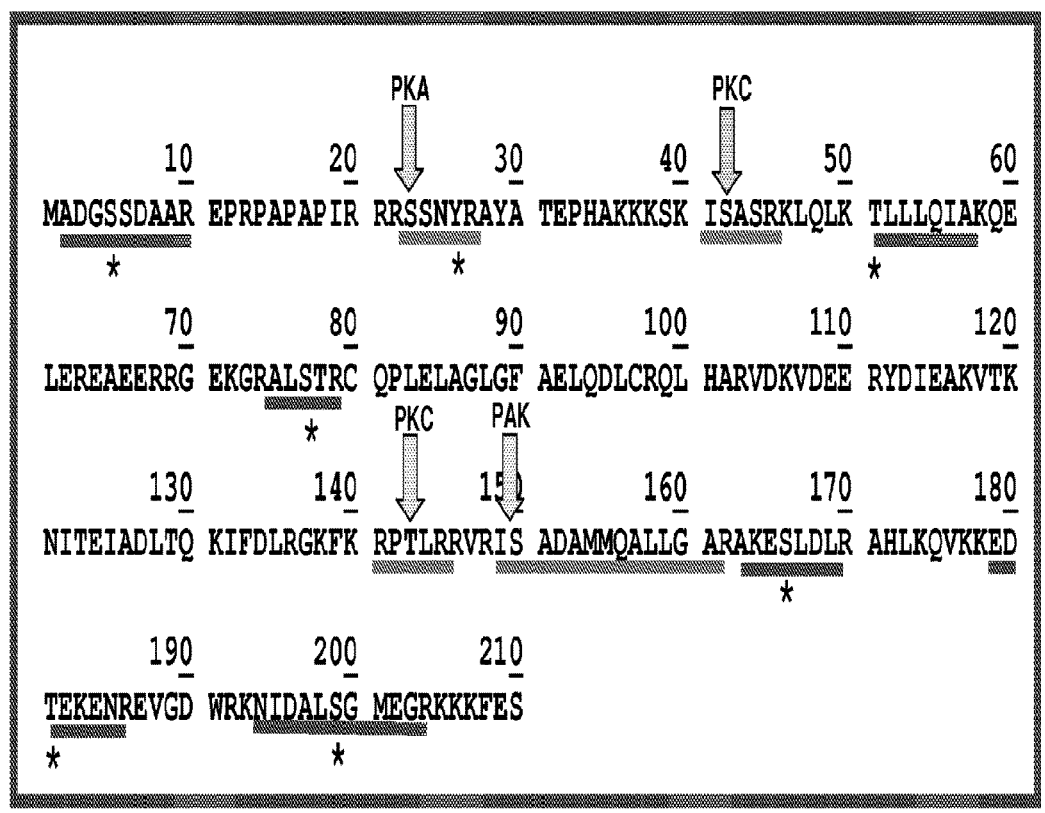

Figure 3. Schematic of multiple phosphorylation residues on human cardiac troponin I. Arrows indicate 6 known phosphorylation residues targeted by different kinases, in which relative peptides are underlined in red. Stars indicate 6 novel phosphorylation residues, in which phosphorylated peptides are underlined in blue. PKA: protein kinase A , PKC: protein kinase C and PAK: p21 activated kinase . Note: using a numbering system including the initiating methionine in the mRNA encoding the molecule.

Figure 5. Example of MRM assay for cTnI phosphopeptide RP(p)TLR

Figure 6. MRM assay for multiply phosphorylated residues of cTnI proteins

Figure 7. Single MRM assay detect novel multiple phosphorylated residues Y25, S165, T180 and S198 of cTnI proteins.

Figure 8.  Monophosphorylated cTnI at S22/23 decreased in ISHD and IDCM.

Figure 9.

| Peptide | Q1 | Q3 | Type | Charge | Observed |
|---|---|---|---|---|---|
| PTLR | | | | | |
| 0 Phospho | 243.656 | 199.1 | b2 | 2+ | Y |
| | 243.656 | 288.2 | y2 | 2+ | Y weak |
| | 243.656 | 389.2513 | y3 | 2+ | YY |
| 1 Phospho | 283.656 | 279.1083 | b2+80 | 2+ | Y |
| | 283.656 | 389.2513 | y4+80 | 2+ | Y |
| | 283.656 | 288.2036 | y2 | 2+ | YY |
| | 283.659 | 392.1924 | b3+80 | 2+ | YYY |
| RPT(p)LR | | | | | |
| 0 Phospho | 321.7068 | 254.1612 | b2 | 2+ | YYYY |
| | 321.7068 | 288.203 | y2 | 2+ | YYYY |
| | 321.7068 | 355.2088 | b3 | 2+ | YYYY |
| | 321.7068 | 389.2507 | y3 | 2+ | YYYY |
| | 321.7068 | 468.2929 | y4 | 2+ | YYYYY |
| 1 Phospho | 361.7068 | 254.1612 | b2 | 2+ | YY |
| | 361.7068 | 288.203 | y2 | 2+ | Y |
| | 361.7068 | 388.203 | y2+80 | 2+ | YYY |
| | 361.7068 | 468.3035 | b4 | 2+ | YY |

Table 2. An example list of MRM transitions for Phosphopeptide containing T142. The more letter Y, the stronger intensity of signal in MRM.

METHODS OF DIAGNOSING AND TREATING HEART FAILURE

CROSS-REFERENCE TO RELATED APPLICATIONS

This application is a 35 U.S.C. § 371 national entry of International Application PCT/US2011/025301 having an international filing date of Feb. 17, 2011, which claims the benefit of U.S. Provisional Application No. 61/305,298, filed Feb. 17, 2010, the content of each of the aforementioned applications is herein incorporated by reference in their entirety.

STATEMENT REGARDING FEDERALLY SPONSORED RESEARCH OR DEVELOPMENT

This invention was made with government support under Grant Nos. HV028180 and HL063038 awarded by the National Institutes of Health. The government has certain rights in the invention.

FIELD OF INVENTION

The invention relates to novel phosphorylation sites in cardiac troponin I, a protein associated with patient risk stratification and the development of heart failure.

BACKGROUND INFORMATION

Despite continuous efforts to find new effective therapies, heart failure (HF) remains one of the most common causes of morbidity and mortality in Western societies. One approach that has been pursued in recent years is the identification of biomarkers to aid in the classification, diagnosis and prognosis of heart failure and other cardiac conditions. In particular, the presence and particular peptides and proteins have been found to be useful diagnostic and prognostic indicators. For example, the phosphorylation of desmin at novel sites has been found to be indicative of an increased risk of heart failure in a patient, as disclosed in International Application No. PCT/US2010/036228, which is incorporated herein by reference.

Investigating individual phosphorylation residues is challenging but essential for understanding cellular signaling and the effect on protein function. To unravel these phosphorylation-dependent structure-function relationships, a quantitative analysis of residue-specific protein phosphorylation and the presence or absence of the N- or C-terminus is required. Phosphorylation of myofilament proteins has been found to play a pivotal role in regulating cardiac contraction. Current approaches to characterize the phosphorylation status are limiting, only able to distinguish one or two different phosphorylated residues within a protein. These techniques rarely allow for a simultaneous, global view of multiple post-translational modified forms (e.g. phosphorylated residues) in a given protein, nor can they provide quantitative information about phosphorylation levels at each residue. Overcoming these limitations will be of major importance for the analysis of a clinically relevant protein such as human cardiac Troponin I (cTnI), a clinical indicator of myocardial damage.

Release of cardiac proteins in the blood, and specifically immunoassay of cTnI in serum is one of the gold standards for diagnosis of acute myocardial infarction. However these diagnostic assays do not specifically assay modifications of the protein which we have associated with heart failure as described in this application. In the heart, cTnI plays a regulatory and inhibitory role as part of the thin filament. It function is regulated by phosphorylation. There are six residues that are known to be phosphorylated by several kinase (Ser$^{23/24}$: target by PKA, PKC, PKD, PKG; Ser$^{42/44}$, Thr$^{143}$: target by PKC; Ser$^{150}$: target by p21-activated kinase (PAK) [1]. The alterations of phosphorylation level on these residues can have dramatic effects on cardiac function and are involved in various cardiac diseases such as cardiac hypertrophy and heart failure (2-4). However, the identification and quantification of multiple phosphorylated residues within the degraded or intact cTnI by immunoassay- or traditional mass spectrometry (MS)-based approach has proven challenging because of the lack of specific antibody to nearly all sites (only PKA and PKC sites are available and they are not to individual sites), high costs along with a long time to develop new specific antibodies, substoichiometric phosphorylation, facile loss of phosphoric acid, variable ionization efficiency with the changing modification status, and the intrinsic molecular complexity of human cTnI. As a result, the basal phosphorylation status of human cTnI has not been adequately established in vivo. Even less is known about the phosphorylation status of cTnI in failing conditions such as Ischemic heart disease (ISHD) and Idiopathic dilated cardiomyopathy (IDCM). To overcome this limitation, our laboratory has developed a MS-based target proteomics quantification method—Multiple Reaction Monitoring (MRM) assay (for more information about MRM see our recent review [5]) for both targeted and global analysis of cTnI, which allows us to systematically identify and quantify the extent of specific post-translational modification including at each potentially phosphorylated residue.

This application claims the benefit of the filing date of provisional patent application no. 61/305,298, filed Feb. 17, 2010, which is incorporated by reference in its entirety herein.

It is understood that the examples and embodiments described herein are for illustrative purposes only and that various modifications or changes in light thereof will be suggested to persons skilled in the art and are to be included within the spirit and purview of this application.

BRIEF DESCRIPTION OF THE DRAWINGS

FIG. 1: An illustration of MRM assay. A) MRM measures peptides unique to a target protein. B) Scheduled MRM™ Algorithm.

FIG. 2: Schematic MRM phosphorylation assay for cardiac troponin I.

FIG. 3: Schematic of multiple phosphorylation residues on human cardiac troponin I. Arrows indicate 6 known phosphorylation residues targeted by different kinases, in which relative peptides are underlined in red. Stars indicate 6 novel phosphorylation residues, in which phosphorylated peptides are underlined in blue. PKA:protein kinase C and PAK: p21 activated kinase. Note: figure uses a numbering system including the initiating methionine in the mRNA encoding the molecule.

FIG. 9: Table 2. An example list of MRM transitions for Phosphopeptide containing T142. The more letter Y, the stronger intensity of signal in MRM.

DESCRIPTION

Figure 4:
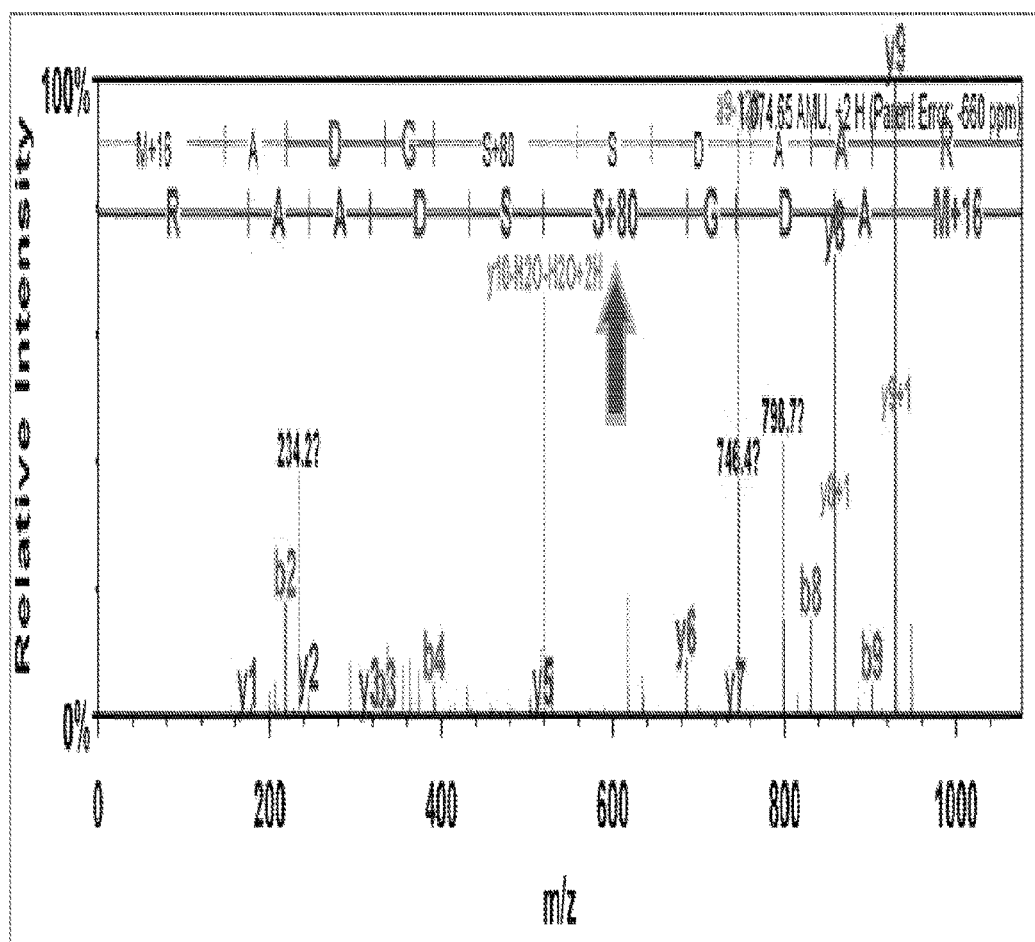
FIG. 4: Identification of phosphorylation residues of recombinant cTni proteins treated by PKA (A-E) and PKCα (F). A) S5-Phosphorylated in MADG(p)SSDAAR; B) S23 and Y26-Phosphorylated in RR(p)SSN(p)YRAYATEPHAK; C) T78-Phosphorylated in ALS (p)TRC-QPLELAGLGFAELQDLCR; D) S166-Phosphorylated in AKE(p)SLDLR; E)S199-Phosphorylated in NIDAL(p)SGMEGR; F)T51-Phosphorylated in (p)TLLLQIAK.
Figure 4:
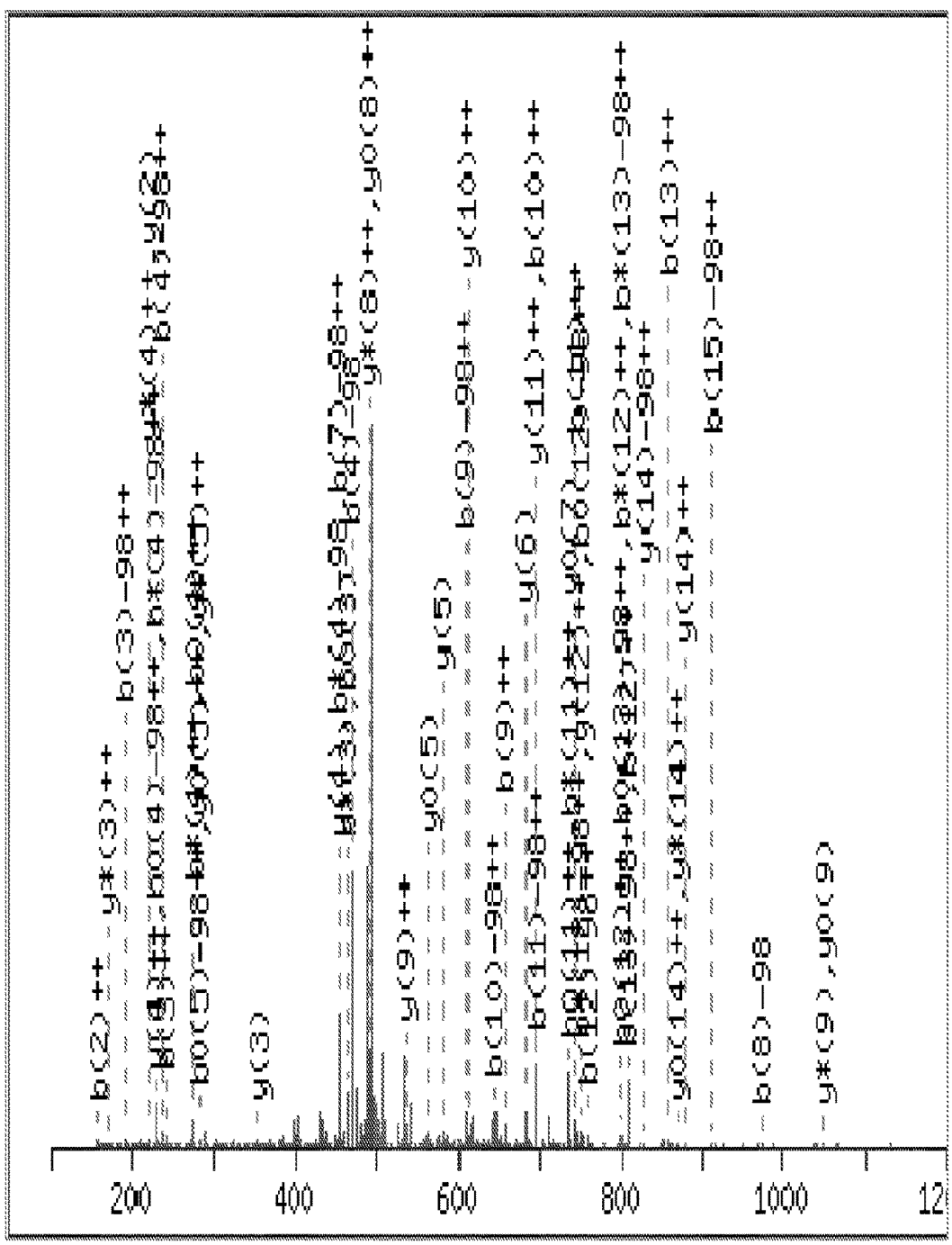
Figure 4:
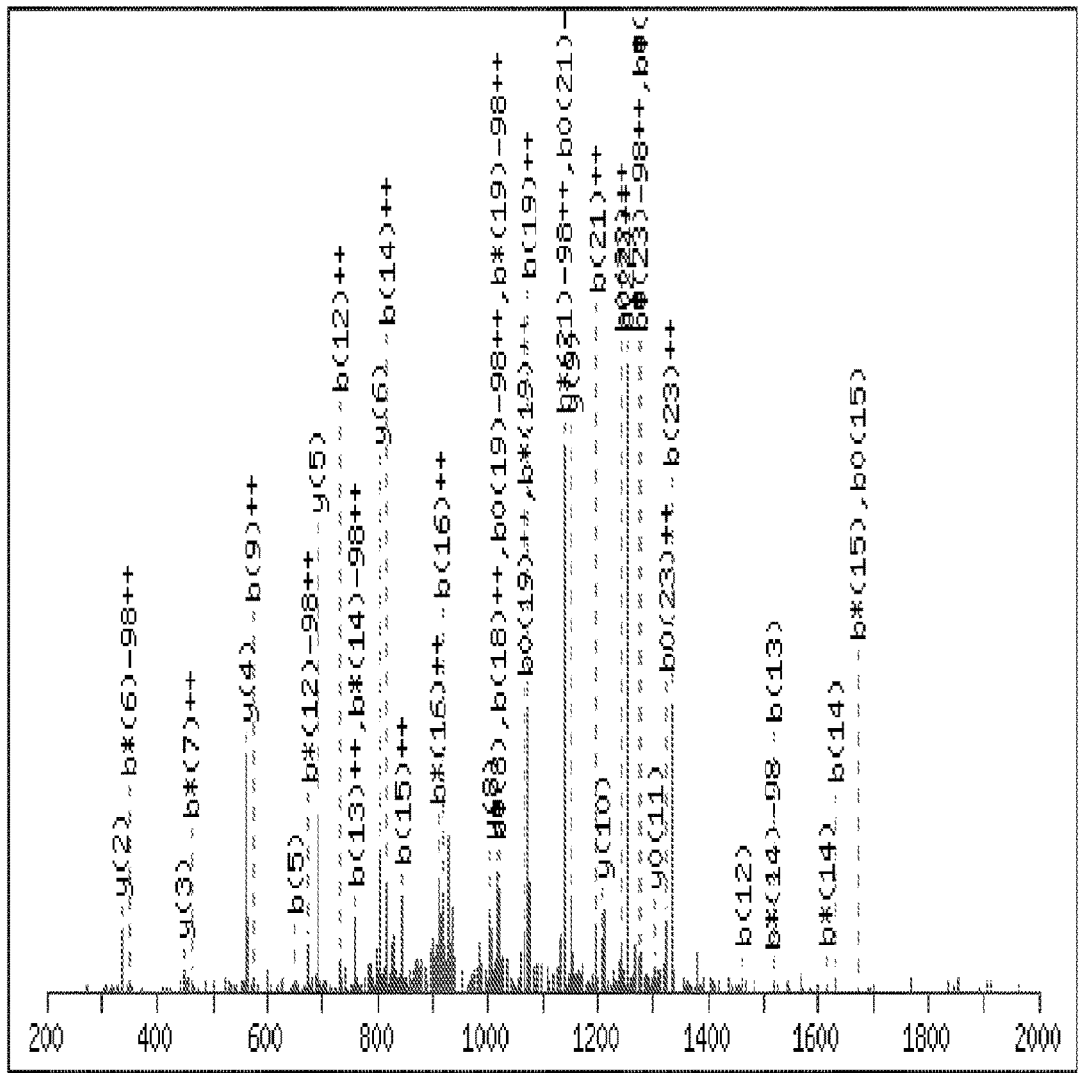
Figure 4:
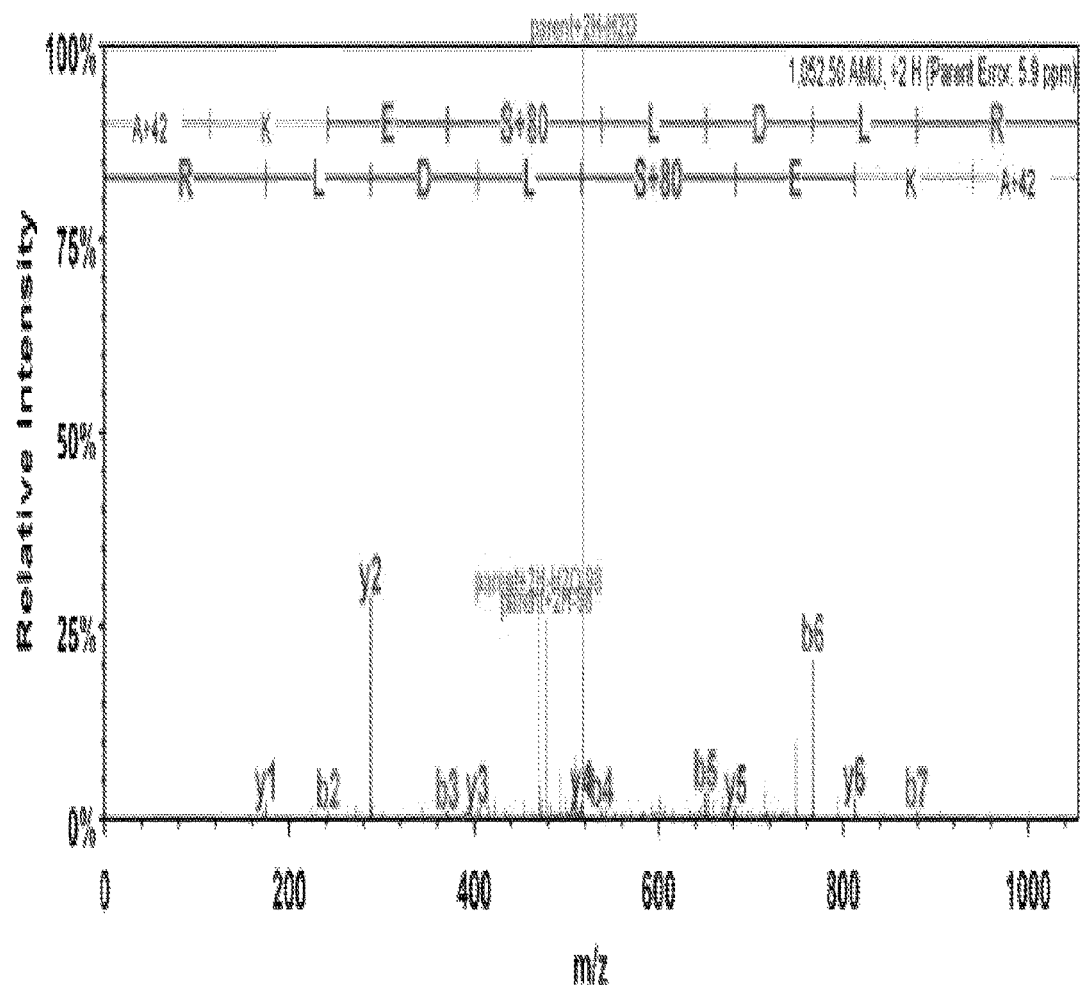
Figure 4:
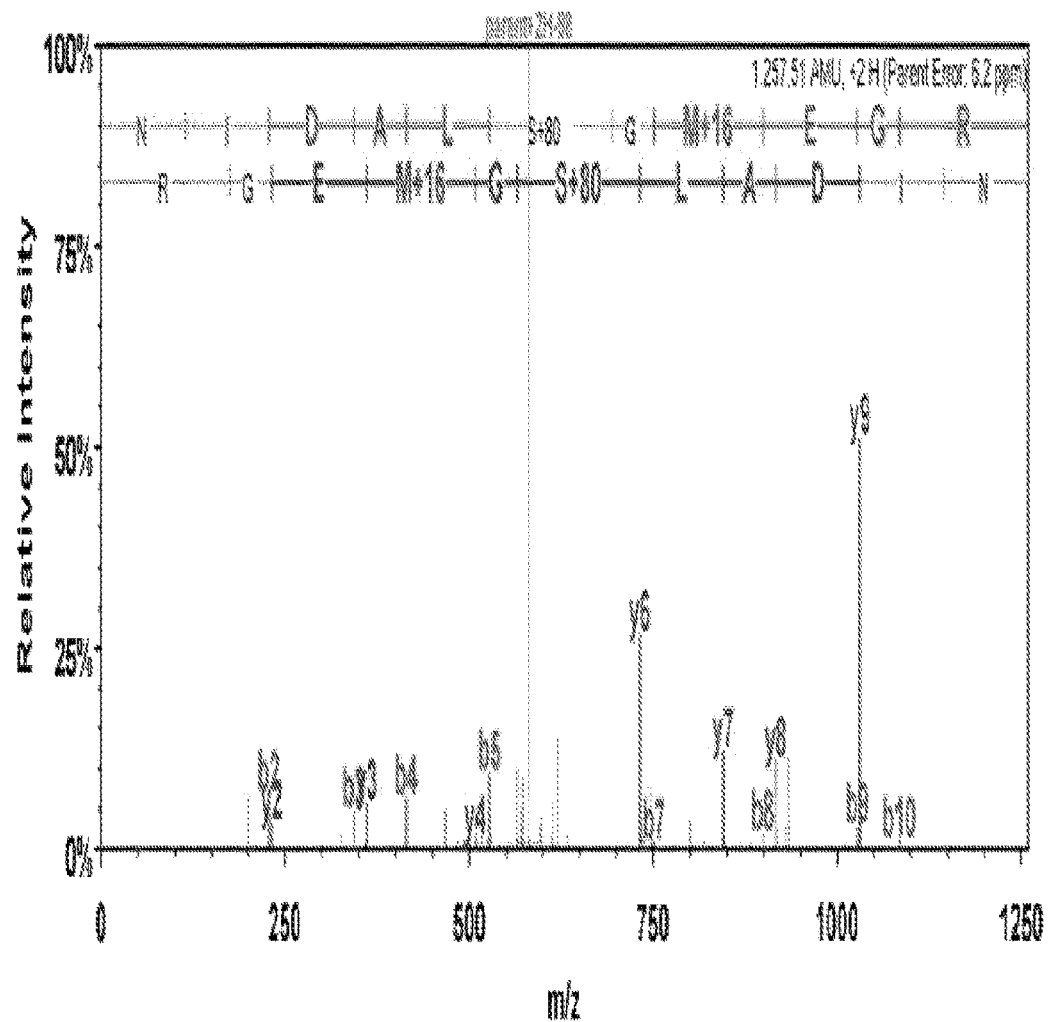
Figure 4:
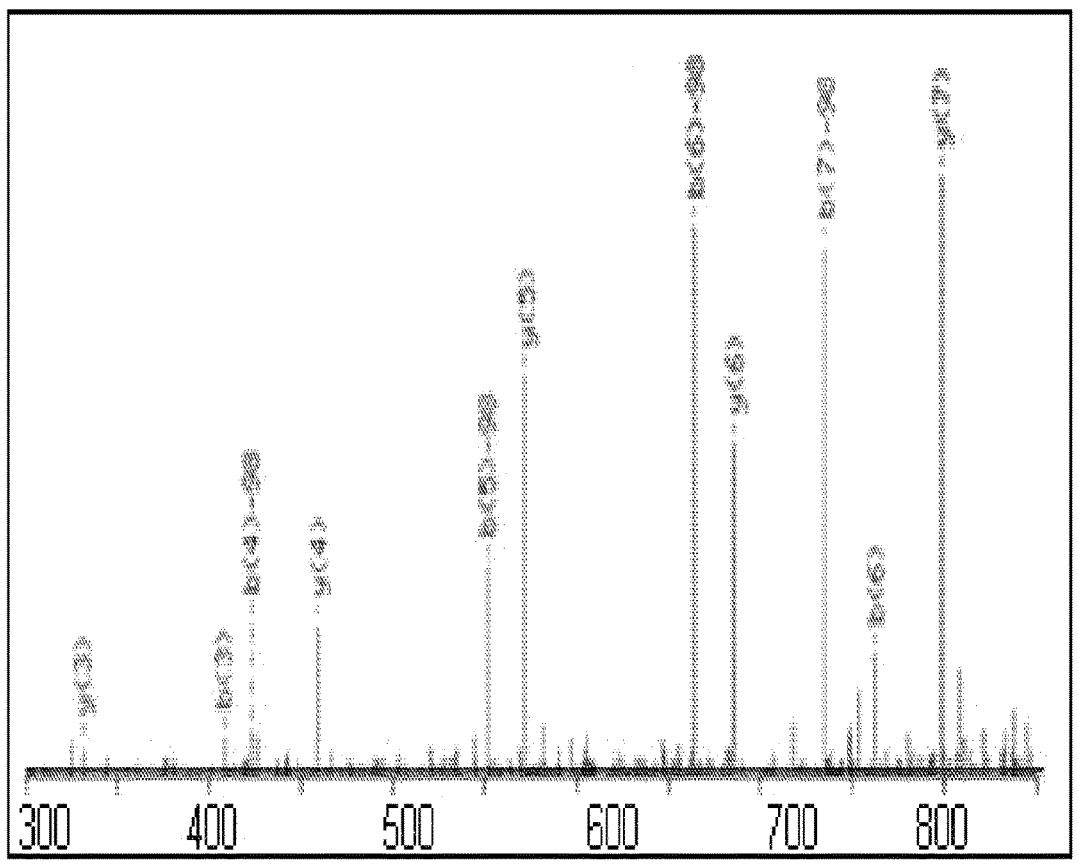

Circulating human cardiac Troponin I (cTnI) is a preclinical and clinical indicator of myocardial damage. Phosphorylation of this cardiac specific myofilament protein plays a pivotal role in regulating the contractile activity of the heart. As we have previously shown that selective proteolysis of the N- and C-terminus of this protein can occur in vivo and alter function. Disclosed herein is a cost-effective, rapid, and sensitive assay(s) that quantifies these post-translational modification including the six known and six additional novel phosphorylated residues of intact or degraded human cardiac Troponin I (cTnI) in healthy and diseased patients and which reflect the functional consequences of the novel sites. Although the inventors are not bound by any particular theory or mechanism, the current hypothesis states that the cTnI phosphorylation status changes with disease, and therefore altered phosphorylation of cTnI at the known and/or our newly identified (novel) sites will impact function and will be reflected in the failing heart disease phenotypes. Until now the major strategies that have been used in measuring this modification are immune-based. This can still be used to detect and quantify individual phosphorylated residues, although it is difficult when sites are situated in close proximity in the sequence. Recently, there has been the development of quantitative mass spectrometry (MS)-based methods that allow the quantification based exclusively on amino acid sequence (and their differences). The former includes radioimmunoassay (RIA) and direct or samwich enzyme-linked immunosorbent assay (ELISA), whereas the latter is applicable directly or to enriched samples. The capture can be done by an enrichment tag (e.g. aptamer, antibody) or based on the physical properties of cTnI or depletion of albumin (or other high abundant proteins). This patent focuses on the detection of the cTnI phosphorylation sites of the intact or degraded protein by either method but outlines in details our newly developed MS-based multiple reaction monitoring (MRM) assay, a multiplex quantitative MS-based method, allows the quantification of one or more of the residue-specific phosphorylation status of cTnI in plasma or serum as well as tissue (e.g. biopsy). Moreover, the assay can provide insight into the role of each modification and could provide diagnostic or prognostic indicators of short and long term outcome.

In one aspect, the present invention is directed to novel phosphorylation sites in cardiac Troponin I, which binds to actin in thin myofilaments to hold the actin-tropomyosin complex in place. The present inventors have demonstrated that certain forms of cardiac Troponin I are present in subjects having heart failure. Specifically, the present inventors have discovered that one or more of the six novel phosphorylated residues of cardiac Troponin I (S5, Y26, T51, S166, T181 and 5199, based on human cTnI sequence including the initiating Methionine, as shown in FIG. 3) may be present during heart failure, in addition to those that were previously known.

Accordingly, in some embodiments of the present invention, it is desirable to use cardiac Troponin I phosphorylation at one or more of the six above-mentioned residues as biomarkers to identify a subject having or being at risk for developing heart failure (risk stratification or prognostic). In some embodiments, a sample is obtained from the subject and the biomarker is detected using a conventional detection method(s) that is well-known in the art. In some embodiments, the biomarker is identified by immunoassay or mass spectrometry. In embodiments, the biomarker is identified by ELISA or immunohistochemistry. In embodiments, the biomarker is detected by Multiple Reaction Monitoring (MRM). In some embodiments, the biomarker is detected by two-dimensional electrophoresis (2DE, separating proteins based on pI and molecular weight), two-dimensional liquid chromatography (2DLC, separating proteins based on pI and hydrophobicity), or one-dimensional liquid chromatography (1DLC, separating proteins based on hydrophobicity). In some embodiments, the biomarker is detected by electron microscopy.

Another aspect of the present invention is a method for determining how to treat a subject suspected of having heart failure, or a subject that is at high risk for developing heart failure (therapeutic monitoring). In some embodiments, a sample is obtained from the subject and the biomarker is detected using conventional detection methods that are well-known in the art. The sample is then compared to a baseline/normal level of cardiac Troponin I phosphorylation. In some embodiments, a subject having increased levels of cardiac Troponin I phosphorylation at one or more of the novel sites S5, Y26, T51, 5166, T181 and/or 5199, either with or without the previously known sites, is determined to have (or is likely to have) heart failure, and is treated with aggressive therapy [such as cardiac resynchronization therapy; heart valve repair or replacement; implantable cardioverter-defibrillator; heart pump; heart transplant; percutaneous coronary intervention (i.e., angioplasty); coronary bypass surgery to replace the injuried/blocked coronary artery; surgical correction of congenital heart defects; or administration of an angiotensin-converting enzyme (ACE) inhibitor, angiotensin II receptor blocker (ARB), digoxin, beta blockers, diuretics, or aldosterone antagonist]. In some embodiments, a subject having normal levels of cardiac Troponin I phosphorylation at S5, Y26, T51, 5166, T181 and/or S199 is determined not to have (or is not likely to have) heart failure, and is treated with non-aggressive therapies [such as administration of aspirin and thrombolysis (e.g., TPA), with periodic monitoring to ensure no future cardiac events; or by recommending changes in life style].

In one embodiment of the invention, the phosphorylation state of S5, Y26, T51, S166, T181 and/or S199 in the Troponin I protein is compared over time to a baseline/normal value and/or to levels known to be associated with heart failure. The kinetic rise and fall of cardiac Troponin I phosphorylation may be indicative of impending heart failure. In some embodiments, the level of cardiacTropinin I phosphorylation at S5, Y26, T51, 5166, T181 and/or S199 is compared over time in a subject receiving treatment. In some embodiments, the baseline value can be based on earlier measurements taken from the same subject, before the treatment was administered.

A method as described above may further comprise measuring in the sample the amount of one or more other markers that have been reported to be diagnostic of heart failure, including (one or more) other cardiac Troponin I phosphorylation sites, such as S23/24, S42/44, T143 and/or S150, cardiac specific isoforms of desmin and/or troponin T (TnT), creatine kinase-MB CK-MB), myoglobin, or brain natriuretic peptide (BNP, or proBNP), ANP, CRP. A significant increase (e.g., at least a statistically significant increase) of the one or more markers is further indicative that the subject is at risk for developing heart failure.

The present invention also provides antibodies that specifically bind to cardiac Troponin I at S5, Y26, T51, 5166, T181 and 5199. In some embodiments, the antibodies specifically bind to un-, mono-, bi-, and/or tri-phosphorylated cardiac Troponin I. In some embodiments, the antibodies are labeled. In some embodiments, the antibodies are labeled with a fluorescent moiety, a moiety that binds a reporter ion, a heavy ion, a gold particle, or a quantum dot. Measurements could determine the amount of phosphorylated sites alone, or the ratio of unphosphorylated to phosphorylated.

The present invention also provides a method of detecting the phosphorylation state of cardiac Troponin I at S5, Y26, T51, 5166, T181 and S199 using conventional detection methods that are well-known in the art. In some embodiments, the method comprises using an antibody that specifically binds to phosphorylated cardiac Troponin I at S5, Y26, T51, 5166, T181 and/or S199. In some embodiments, the antibodies specifically bind to un-, mono-, bi-, and/or tri-phosphorylated cardiac Troponin I. In some embodiments, the antibodies are labeled. In some embodiments, the antibodies are labeled with a fluorescent moiety, a moiety that binds a reporter ion, a heavy ion, a gold particle, or a quantum dot.

Another aspect of the invention is a kit for identifying a subject at risk for developing heart failure. In some embodiments, the kit contains an agent that detects the phosphorylation state of cardiac Troponin I at S5, Y26, T51, 5166, T181 and 5199. In some embodiments, the kit contains an antibody that detects the level of Troponin I phosphorylation at S5, Y26, T51, 5166, T181 and 5199. In some embodiments, the antibody specifically binds to un-, mono-, bi-, and/or tri-phosphorylated cardiac Troponin I or fragment thereof. In some embodiments, the antibody is labeled. In some embodiments, the antibody is labeled with a fluorescent moiety, a moiety that binds a reporter ion, a heavy ion, a gold particle, or a quantum dot.

In some embodiments, the sample is analyzed by mass spectrometry. As such, in some embodiments, the kit contains labeled peptides (synthetic or recombinant). Also provided is an MRM assay for determining the phosphorylation status of the identified residues of cardiac Troponin I. This may be a measure of phosphorylated sites alone, a measure of phosphorylated to unphosphorylated ratio for those residues, a measure of the above with respect to total TnI (measure by a different unmodifiable MRM assay), or any combination thereof.

Current approaches to characterize the phosphorylation status are limited, only able to distinguish one or two different phosphorylated residues within a protein. The MRM assay has novel features include 1) a possible replacement for immunoassay such as ELISA (although immunoassays to the unphosphorylated and phosphorylated residues of each of the novel phosphorylation sites could be made) in screening for HF and other cardiac injuries including stroke, toxicity, heart surgery and transplantation. 2) a simultaneous, global view of multiple phosphorylated residues in a given protein; 3) multiplex quantitative information about phosphorylation levels at each residue; 4) simultaneous monitoring of each phosphorylated—and unphosphorylated-site of biomarkers such as cTnI; 5) multiplexed quantification of proteins and peptides in complex matrixes such as HF tissues without the need for antibodies; 6) the dynamic detection and validation of phosphorylation change in the time-course of in vitro kinase or phosphatase treatment and the in vivo underlying relationship between phosphorylation and heart failure; 7) a simultaneous validation and quantification of both the known and the novel phosphorylated residues. Using the MRM assay, we can assess the all six known phosphorylated residues independently (S23/24, S42/44, T143 and S150) as well as the total amount of cTnI (based on unmodifiable peptide). Moreover, we have made fundamental new discoveries about the phosphorylation of cTnI, including 1) the identification of six novel phosphorylated residues (S5, Y26, T51, S166, T181 and S199) and 2) that the cTnI endogenous phosphorylation status of some, but not all, phosphorylated residues is significantly decreased in ischemic heart disease (ISHD) and idiopathic dilated cardiomyopathy (IDCM) compared to the non-failing donor heart.

The known protein kinase A (PKA)-mediated phosphorylation sites (S23 and S24) lie within the cardiac-specific N-terminal (residues 1-32) which interacts with the N-domain of cTnC. Our MRM assay showed that these sites are significantly decreased phosphorylation in HF when compared to the non-failing donor heart (the ratio of phosphorylation to unphosphorylation in Donor:ISHD:IDCM=0.136:0.039; 0.014; each type, n=10). This result was compatible with the decreased trend of phosphorylation in HF by western blotting analysis using S23/24 site-specific phosphorylated antibodies (ISHD ↓, 35.43%, p<0.001 and IDCM ↓88.90%, p<0.001). A similar decline was found at the novel site Y26 (0.563:0.254:0.232) and S5 (0.36:0:0) due to their locations on the interaction region between cTnI and cTnC. By contrast, phosphorylation in HF was higher on the known PKC sites S42 (0.154:0.244:0.122) and T143 (2.326: 3.36:4.044), and the unknown site S77 (0.575:1.147:0.887) as compared to donor heart; a relative higher ratio of cTnI phosphorylation in HF was also found on novel sites S166 (0.0107:0.0143:0.0344), T181 (0.1428:0.2044:0.2207) and S199 (0.0047:0.0142:0.0103). The phosphorylation of Thr-143 (known) and Ser-199 (novel) by PKCα may lower $Ca^{2+}$-sensitivity of force development.

Thus, we propose that MRM of one or more of the novel phosphorylation sites alone or in combination with one or more of the know phosphorylation sites will allow risk stratification of heart patients and therapeutic monitoring. The detection can be done by using antibodies to the phosphorylated and unphosphorylated cTnI but also by using MRM to the specific phosphorylated or unphosphorylated peptides. As well, peptides to the N- or C-terminus could be included and used to assess whether the intact or degraded protein is phosphorylated and a peptide to an unmodifiable peptide(s) that can be used to quantify the concentration of total TnI.

The diagnostic assay will be used for diagnosis, prognosis or risk stratification in patients with cardiac disease. Generally, 33% of patients that have a myocardial infarction (MI, circulating cTnI positive) end up with heart failure (HF) within 1-2 years, but there is currently no way to know which patients are at risk of HF and other complications (such as stroke, re-hospitalization). In addition, patients undergoing heart surgery and those receiving toxic drugs such as in cancer chemotherapy as well as other cardiac injuries such as ischemic injury to the donor heart prior to heart transplantation also have associated risk and again there is no mechanism for differentiating the patient groups.

Therefore, treatment regime cannot be tailored for each individual. Detection and quantification of various modifications including phosphorylation at different amino acid residues (or degradation), resulting from disease, toxicity and other cardiac injuries, can yield surrogate markers for functional recovery and clinical outcome individually.

To facilitate an understanding of the present invention, a number of terms and phrases are defined below.

As used herein, the singular forms "a", "an", and "the" include plural forms unless the context clearly dictates otherwise. Thus, for example, reference to "a protein" includes reference to more than one protein.

As used herein, "heart failure" refers to a condition in which a subject experiences inadequate blood flow to fulfill the needs of the tissues and organs of the body. Heart failure has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of heart failure are present even at rest and where increased discomfort is experienced with any physical activity. As such, heart failure includes cardiac-related illnesses such as myocardial infarction, ischemic heart disease, hypertension, valvular heart disease, and cardiomyopathy.

A sample which is "provided" can be obtained by the person (or machine) conducting the assay, or it can have been obtained by another, and transferred to the person (or machine) carrying out the assay.

By a "sample" (e.g. a test sample) from a subject is meant a sample that might be expected to contain elevated levels of the protein markers of the invention in a subject having heart failure. Many suitable sample types will be evident to a skilled worker. In some embodiments, the sample is a blood sample, such as whole blood, plasma, or serum (plasma from which clotting factors have been removed). For example, peripheral, arterial or venous plasma or serum can be used. In some embodiments, the sample is urine, sweat, or another body fluid into which proteins are sometimes removed from the blood stream. In the case of urine, for example, the protein is likely to be broken down, so diagnostic fragments of the proteins of the invention can be screened for. In some embodiments, the sample is cardiac tissue, which is harvested, e.g., after a heart transplant or the insertion of a pacemaker or defibrillator. In some embodiments, the tissue is tissue slices or tissue homogenates. Methods for obtaining samples and preparing them for analysis (e.g., for detection of the amount of protein) are conventional and are well-known in the art.

A "subject," as used herein, includes any animal that has, or is at risk of developing, heart failure. Suitable subjects (patients) include laboratory animals (such as mouse, rat, rabbit, guinea pig or pig), farm animals, sporting animals (e.g., dogs or horses), domestic animals, and pets (such as a horse, dog or cat). Non-human primates and human patients are included. For example, human subjects who present with chest pain or other symptoms of cardiac distress, including, e.g., shortness of breath, nausea, vomiting, sweating, weakness, fatigue, or palpitations, can be evaluated by a method of the invention. In addition, subjects not exhibiting these symptoms can also be evaluated by a method of the present invention. Some subjects at risk for developing heart failure (e.g., subjects with myocardial infarction) do not experience symptoms such as chest pain. Furthermore, patients who have been evaluated in an emergency room, in an ambulance, or in a physician's office and are dismissed as not being ill according to current tests for heart failure can have an increased risk of having a heart attack in the next 24-48 hours. Such patients can be monitored by a method of the invention to determine if and when they begin to express markers of the invention, indicating that the subject is now at risk for developing heart failure. Subjects can also be monitored by a method of the invention to improve the accuracy of current provocative tests for assessing the risk of developing heart failure, such as exercise stress testing. An individual can be monitored by a method of the invention during exercise stress tests to determine if the individual is at risk for developing heart failure; such monitoring can supplement or replace the test that is currently carried out. Athletes (e.g., humans, racing dogs or race horses) can be monitored during training to ascertain if they are exerting themselves too vigorously and are in danger of developing heart failure.

"At risk of" is intended to mean at increased risk of, compared to a normal subject, or compared to a control group, e.g., a patient population. Thus, a subject carrying a particular marker may have an increased risk for a specific disease or disorder, and be identified as needing further testing. "Increased risk" or "elevated risk" mean any statistically significant increase in the probability, e.g., that the subject has the disorder.

Although much of the data presented in the Examples herein are directed to particular forms of cardiac Troponin I (or peptides or fragments thereof), it will be evident to a skilled worker that a variety of forms of these proteins may be indicative of the risk of developing heart failure in a subject. For example, the protein may be an intact, full-length cardiac Troponin I. In addition, as discussed in detail below, degraded and/or fragmented forms of cardiac Troponin I are also associated with myocardial infarction. In such a case, an investigator can determine the level of one or more of the fragments or degradation products. Furthermore, when cardiac Troponin I undergoes processing naturally (e.g., posttranslational modifications, such as acetylation, methylation, phosphorylation, etc.), any of these forms of the protein are included in the invention. As such, "cardiac Troponin I" refers to full-length cardiac Troponin I, a fragment of cardiac Troponin I, and posttranslationally modified forms of cardiac Troponin I. Useful fragments include, for example, amino acid residues 1-193, 63-193, 73-193, 1-62, 1-72 in rat and 1-193, 63-193, 73-193 and 1-62, 1-72 in human. (For the human sequence this includes the initial Met as shown in FIG. 3).

A variety of tests have been used to detect heart failure. These include, e.g., determining the levels of cardiac specific isoform(s) or modified forms of troponin I (TnI) and/or troponin T (TnT), CK-MB (Creatine Kinase-MB), myoglobin, desmin and brain natriuretic peptide (BNP). Atrial natriuretic peptide (ANP), soluble interleukin 1 like receptor (sST2) However, none of these markers is completely satisfactory for the detection of heart failure. For example, they can fail to detect early stages of heart failure, such as non-necrotic myocardial ischemia. The new markers described herein can be used in conjunction with these types of assays.

When the values of more than one protein are being analyzed, a statistical method such as multi-variant analysis or principal component analysis (PCA) is used which takes into account the levels of the various proteins (e.g., using a linear regression score). For verification, we will use either an immunoassay or a multiple reaction monitoring (MRM, a MS-based targeted method that quantifies peptides that are unique to the protein of interest).

In some embodiments, it is desirable to express the results of an assay in terms of an increase (e.g., a statistically significant increase) in a value (or combination of values) compared to a baseline value.

A "significant" increase in a value, as used herein, can refer to a difference which is reproducible or statistically significant, as determined using statistical methods that are appropriate and well-known in the art, generally with a probability value of less than five percent chance of the change being due to random variation. In general, a statistically significant value is at least two standard deviations from the value in a "normal" healthy control subject. Suitable statistical tests will be evident to a person of ordinary skill in the art. For example, a significant increase in the amount of a protein compared to a baseline value can be about 50%, 2-fold, or more higher. A significantly elevated amount of a protein of the invention compared to a suitable baseline value, then, is indicative that a test subject has a risk of developing heart failure. A subject is "likely" to to be at risk for developing heart failure if the subject has levels of the marker protein(s) significantly above those of a healthy control or his own baseline (taken at an earlier time point). The extent of the increased levels correlates to the % chance. For example, the subject can have greater than about a 50% chance, e.g., greater than about 70%, 80% 90%, 95% or higher chance, of developing heart failure. In general, the presence of an elevated amount of a marker of the invention is a strong indication that the subject has heart failure.

As used herein, a "baseline value" generally refers to the level (amount) of a protein in a comparable sample (e.g., from the same type of tissue as the tested tissue, such as blood or serum), from a "normal" healthy subject that does not have heart failure. If desired, a pool or population of the same tissues from normal subjects can be used, and the baseline value can be an average or mean of the measurements. Suitable baseline values can be determined by those of skill in the art without undue experimentation. Suitable baseline values may be available in a database compiled from the values and/or may be determined based on published data or on retrospective studies of patients' tissues, and other information as would be apparent to a person of ordinary skill implementing a method of the invention. Suitable baseline values may be selected using statistical tools that provide an appropriate confidence interval so that measured levels that fall outside the standard value can be accepted as being aberrant from a diagnostic perspective, and predictive of heart failure.

It is generally not practical in a clinical or research setting to use patient samples as sources for baseline controls. Therefore, one can use any of variety of reference values in which the same or a similar level of expression is found in a subject that does not have heart failure.

It will be appreciated by a person of ordinary skill in the art that a baseline or normal level need not be established for each assay as the assay is performed, but rather, baseline or normal levels can be established by referring to a form of stored information regarding a previously determined baseline levels for a given protein or panel of proteins, such as a baseline level established by using any of the methods described herein. Such a form of stored information can include, for example, a reference chart, listing or electronic file of population or individual data regarding "normal levels" (negative control) or positive controls; a medical chart for the patient recording data from previous evaluations; a receiver-operator characteristic (ROC) curve; or any other source of data regarding baseline levels that is useful for the patient to be diagnosed. In some embodiments the amount of the proteins in a combination of proteins, compared to a baseline value, is expressed as a linear regression score, as described, e.g., in Irwin, in Neter, Kutner, Nachtsteim, Wasserman (1996) Applied Linear Statistical Models, 4th edition, page 295.

In some embodiments in which the progress of a treatment is being monitored, a baseline value can be based on earlier measurements taken from the same subject, before the treatment was administered.

The amount of a protein can be measured using any suitable method. Some methods involve the use of antibodies, binding ligands, or mass spectrometry tagged peptides specific for a protein of interest. Antibodies suitable for use in assays of the invention are commercially available, or can be prepared routinely. Methods for preparing and using antibodies in assays for proteins of interest are conventional, and are described, e.g., in Green et al., Production of Polyclonal Antisera, in *Immunochemical Protocols*, Manson ed. (Humana Press 1992); Coligan et al., in *Current Protocols in Immunology*, sections 2.4.1 and 2.5.1-2.6.7 (1992); Kohler & Milstein, *Nature* 256:495-7 (1975); and Harlow et al., Antibodies: A Laboratory Manual, page 726 (Cold Spring Harbor Laboratory Pub. 1988). We can also use MRM assay to a nonmodified region of cTnI.

Immortalized human B lymphocytes immunized in vitro or isolated from an immunized individual that produce an antibody directed against a target antigen can be generated. See, e.g., Cole et al., *Monoclonal Antibodies and Cancer Therapy*, Alan R. Liss ed., p. 77 (1985); Boemer et al., *J Immunol*, 147 (1):86-95 (1991); and U.S. Pat. No. 5,750,373. Also, the human antibody can be selected from a phage library, where that phage library expresses human antibodies, as described, for example, in Vaughan et al., *Na. Biotech*, 14:309-314 (1996), Sheets et al., *Proc Natl Acad Sci*, 95:6157-6162 (1998), Hoogenboom and Winter, 1991, *J Mol. Biol.*, 227:381, and Marks et al., *J Mol Biol*, 222:581 (1991). Techniques for the generation and use of antibody phage libraries are also described in U.S. Pat. Nos. 5,969,108, 6,172,197, 5,885,793, 10 6,521,404; 6,544,731; 6,555,313; 6,582,915; 6,593,081; 6,300,064; 6,653,068; 6,706,484; and 7,264,963; and Rothe et al., *J Mol Bio, J Mol Biol* 376:1182-1200 (2007). Affinity maturation strategies, such as chain shuffling (Marks et al., *Bio/Technology* 10:779-783 (1992)), are known in the art and may be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

Any of a variety of antibodies can be used in methods of the invention. Such antibodies include, e.g., polyclonal, monoclonal (mAbs), recombinant, humanized or partially humanized, single chain, Fab, and fragments thereof. The antibodies can be of any isotype, e.g., IgM, various IgG isotypes such as $IgG_1$, $IgG_{2a}$, etc., and they can be from any animal species that produces antibodies, including goat, rabbit, mouse, chicken or the like. The term, an antibody "specific for" or that "specifically binds" a protein, means that the antibody recognizes a defined sequence of amino acids, or epitope in the protein. An antibody that is "specific for," "specifically recognizes," or that "specifically binds" a polypeptide refers to an antibody that binds selectively to the polypeptide and not generally to other polypeptides unintended for binding to the antibody. The parameters required to achieve such specificity can be determined routinely, using conventional methods in the art. Conditions that are effective for binding a protein to an antibody which is specific for it are conventional and well-known in the art.

"Detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, flow cytometry, or direct analysis by mass spectrometry of intact or subsequentally digested peptides (one or more peptide can be assessed). Persons of skill in the art are familiar with techniques for labelling compounds of interest, and means for detection.

A "fragment" or "peptide" of a protein, e.g. cardiac Troponin I, generally refers to an amino acid sequence between 4 and 30 residues in length, e.g. 5, 6, 7, . . . 28, 29 or 30 residues.

For example, the following peptides can be used for monitoring phosphorylation sites of cTnI:
Ac-ADGSSDAAR (S5/6-unphospho), Ac-ADG(p)SS-DAAR (S5-nonphos), Ac-ADGS(p)SDAAR-OH (S6-monophos), Ac-ADG(p)S(p)SDAAR (S5 and S6-diphos), SSNYR (S22/23-unphospho), (p)SSNYR(S23-monophos), S(p)SNYR (S24-monophos), (p)S(p)SNYR (S23 and S24-diphos), SSN(p)YR (Y26-monophos), ISASR (S42/44-unphospho), I(p)SASR (S42-monophos), ISA(p)SR (S44-monophos), I(p)SA(p)SR (S42 and S44-diphos), TLLLQIAK T51-unphospho), (p)TLLLQIAK (T51-mono-phospho), ALSTR (S76/T77-unphospho), AL(p)STR(S76-monophospho), ALS(p)TR (T77-monophospho), AL(p)S(p)TR (S76/T77-diphospho), RPTLR (T143-unphospho), RP(p)TLR(T143-monophospho), ISADA(oxi)M(oxi)MQALLGAR or ISADAMMQALLGAR (S150-unphospho), I(p)SADA(oxi)M(oxi)MQALLGA or I(p)SADAM-MQALLGAR (S150-monophospho), AKESLDLR (S166-unphospho), AKE(p)SLDLR(S166-monophospho), EDTEK (T181-unphospho), ED(p)TEK (T181-monphospho), NID-ALSGMEGR(S199-unphospho), NIDAL(p)SGMEGR (S199-monophospho), and the peptide NITEIADLTQK* (for a total quantification).

In one embodiment of the invention, antibodies specific for a (one or more) protein of 30 the invention are immobilized on a surface (e.g., are reactive elements on an array, such as a microarray, or are on another surface, such as used for surface plasmon resonance (SPR)-based-technology, such as BIAcore), and proteins in the sample are detected by virtue of their ability to bind specifically to the antibodies. Alternatively, proteins in the sample can be immobilized on a surface, and detected by virtue of their ability to bind specifically to the antibodies. Methods of preparing the surfaces and performing the analyses, including conditions effective for specific binding, are conventional and well-known in the art.

Among the many types of suitable immunoassays are competitive and non-competitive assay systems using techniques such as BIAcore analysis, FACS analysis, immunofluorescence, immunohistochemical staining, Western blots (immunobots), radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, fluorescence-activated cell sorting (FACS), protein A immunoassays, etc. Assays used in a method of the invention can be based on colorimetric readouts, fluorescent readouts, mass spectrometry, visual inspection, etc. Assays can be carried out, e.g., with suspension beads, or with arrays, in which antibodies or cell or blood samples are attached to a surface such as a glass slide or a chip.

In one embodiment, a tissue sample (e.g. a cardiac tissue sample) is stained with a suitable antibody in a conventional immunohistochemical assay for those proteins which are present in the myocardium.

Mass spectrometry (MS) can also be used to determine the amount of a protein, using conventional methods. Some such typical methods are described in the Examples herein. Relative ratio between multiple samples can be determined using label free methods, based on spectral count (and the number of unique peptides and the number of observation of each peptide). Alternatively, quantitive data can be obtained using multiple reaction monitoring (MRM), most often carried out using a triple quadrupole mass spectrometer. In this case, peptides that are unique to a given protein are selected in the MS instrument and quantified.

Absolute quantification can be obtained if a known labeled synthetic peptide (e.g., $^{15}$N) is used. For detailed methods see, e.g., Qin Fu and JE Van Eyk, in *Clinical Proteomics: from diagnostics to therapy*, Van Eyk JE and Dunn M, eds, (Wiley and Son Press 2008); and Gundry et al., Preparation of Proteins and Peptides for Mass Spectrometry Analysis in a Bottom-Up Proteomics Workflow, *Current Protocols in Molecular Biology*, Ausubel et al. eds., (John Wiley & Sons, Inc., Oct 2009).

In general, molecular biology methods referred to herein are well-known in the art and are described, e.g., in Sambrook et al., Molecular Cloning: A Laboratory Manual, current edition, Cold Spring Harbor Laboratory, Cold Spring Harbor, N.Y., and Ausubel et al., Current Protocols in Molecular Biology, John Wiley & Sons, New York, N.Y.

"Diagnostic" means identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A detection (diagnostic) method of the invention can be adapted for many uses. For example, it can be used to follow the progression of heart failure. In one embodiment of the invention, the detection is carried out both before (or at approximately the same time as), and after, the administration of a treatment, and the method is used to monitor the effectiveness of the treatment. A subject can be monitored in this way to determine the effectiveness for that subject of a particular drug regimen, or a drug or other treatment modality can be evaluated in a preclinical or clinical trial. If a treatment method is successful, the levels of the protein markers of the invention are expected to decrease.

The markers can also be used for risk stratification or as prognostic indicators, subjects with "unfavorable" profiles (e.g. having decreased levels of phosphorylated biomarker) being at higher risk and/or having poorer prognoses than subjects with normal levels. As described herein, such subjects can be monitored more closely or treated more aggressively than subjects not having such indications.

As used herein, "treated" means that an effective amount of a drug or other anti-heart failure procedure is administered to the subject. An "effective" amount of an agent refers to an amount that elicits a detectable response (e.g. of a therapeutic response) in the subject.

One aspect of the invention is a kit for detecting whether a subject is at risk for developing heart failure, comprising one or more agents for detecting the amount of a protein of the invention. In some embodiments, other markers for heart failure (e.g., as discussed elsewhere herein) can also be present in a kit. The kit may also include additional agents suitable for detecting, measuring and/or quantitating the amount of protein, including conventional analytes for creation of standard curves. Among other uses, kits of the invention can be used in experimental applications. A person of ordinary skill in the art will recognize components of kits suitable for carrying out a method of the present invention.

If mass spectrometry is to be used to measure protein levels, the following reagents can be included in the kit: known amounts of a labeled (e.g. stable isotope or unlabeled but scrambled in sequence) peptide (synthetic or recombinant) standard for each peptide to be assessed, separately or combined into a single mixture containing all peptides; optionally, a different peptide standard for assessing reproducibility of the assay; and/or, optionally, dilutant and trypsin for preparation of the sample. Kits for mass spectrometry are conventional and well-known in the art. A person of ordinary skill in the art will recognize components of kits suitable for detecting a biomarker(s) using mass spectrometry.

If an antibody-based method is to be used to measure protein levels, the agents in the kit can encompass antibodies specific for the proteins. In some embodiments, the antibodies are labeled with a detectable marker, e.g., a chemiluminescent, enzymatic, fluorescent, or radioactive moiety. In some embodiments, the kit includes a labeled binding partner(s) to the antibodies. Antibody-based kits for protein detection are conventional and well-known in the art. A person of ordinary skill in the art will recognize components of kits suitable for detecting a biomarker(s) using antibodies.

In some embodiments, a kit of the invention may comprise instructions for performing the method. Optionally, the kit can include instructions for taking a sample from the mammalian subject (e.g., body fluid), and using the kit to identify a mammalian subject at risk of developing heart failure. In some embodiments, a kit of the invention contains suitable buffers, containers, or packaging materials. The reagents of the kit may be in containers in which the reagents are stable, e.g., in lyophilized form or stabilized liquids. The reagents may also be in single use form, e.g., for the performance of an assay for a single subject.

Embodiments of the present invention can be further defined by reference to the following non-limiting examples, which describe the methodology employed to identify and characterize novel phosphorylation sites on cardiac Troponin I that are linked to the molecular mechanism of heart failure. It will be apparent to those skilled in the art that many modifications, both to materials and methods, may be practiced without departing from the scope of the present disclosure.

EXAMPLES

Methods
Tissue Samples

Human Left ventricular (LV) transmural tissue samples were obtained from patients with end-stage ISHD (n=10), IDCM (n=10) and non-failing donor hearts (n=10) (Table 1). The tissue from these deidentified tissue banked samples was collected in cardioplegic solution and stored in liquid nitrogen. The samples were provided to us by Dr. Cris Dos Remoidois, University of Sidney, Australia.

TABLE 1

Characteristics of Human Heart Failure Samples

| Code # | Type | ID # | SEX | AGE | LVEF (%) | NYHA |
|---|---|---|---|---|---|---|
| 1 | ISHD | 3.062 | M | 31 | 23 | — |
| 2 | ISHD | 3.007 | M | 45 | — | IV |
| 3 | ISHD | 2.063 | M | 46 | 25 | — |
| 4 | ISHD | 3.123 | M | 47 | 20 | — |
| 5 | ISHD | 3.078 | M | 50 | — | — |
| 6 | ISHD | 3.106 | M | 52 | — | III/IV |
| 7 | ISHD | 3.105 | M | 54 | — | — |
| 8 | ISHD | 3.143 | M | 54 | — | III/IV |
| 9 | ISHD | 3.075 | F | 43 | — | III |
| 10 | ISHD | 3.103 | F | 49 | — | — |
| 11 | IDCM | 2.092 | M | 43 | — | IV |
| 12 | IDCM | 3.104 | M | 46 | — | II |
| 13 | IDCM | 3.138 | M | 56 | 15 | IV |
| 14 | IDCM | 2.095 | M | 57 | 10 | — |
| 15 | IDCM | 4.098 | M | 58 | 20 | III/IV |
| 16 | IDCM | 4.058 | M | 60 | 15 | — |
| 17 | IDCM | 3.096 | F | 23 | 15 | III |
| 18 | IDCM | 3.159 | F | 31 | 20 | — |
| 19 | IDCM | 2.111 | F | 53 | 20 | — |
| 20 | IDCM | 2.115 | F | 54 | 22 | III |
| 21 | Donor | 4.015 | M | 19 | — | — |
| 22 | Donor | 2.152 | M | 23 | — | — |
| 23 | Donor | 4.013 | M | 23 | — | — |
| 24 | Donor | 3.135 | M | 26 | — | — |
| 25 | Donor | 3.145 | M | 39 | — | — |
| 26 | Donor | 2.149 | M | 44 | — | — |
| 27 | Donor | 3.141 | M | 52 | — | — |
| 28 | Donor | 3.084 | F | 27 | — | — |
| 29 | Donor | 3.073 | F | 41 | — | — |
| 30 | Donor | 3.056 | F | 45 | — | — |

LVEF: left ventricular ejection fraction;
NYHA: New York Heart Association;
Functional Classification of classifying the extent of heart failure Myofilament Protein Extraction
Cardiac myofibrils were prepared according to myofilament-enriched extract method [39].
In Vitro Phosphorylation Assay
In Vitro PKA Phosphorylation
In vitro PKA Phosphorylation was performed essentially according to the method as described previously [32]. Briefly, myofibrils were suspended in a 50 µl reaction volume of standard relaxing solution (mM: 60 imidazole, 14.4 KCl, 8.2 MgCl2, 5.5 ATP, 10 EGTA, pH 7.0) containing 30 U of the PKA catalytic subunit, and in vitro phosphorylation was carried out at room temperature for 1 h.

In Vitro PKC Phosphorylation

PKCα- and PKCε-mediated phosphorylation on myofilaments was done according to the method described in [40].

Dephosphorylation of Myofibrils with Phosphatases

Completion of the dephosphorylation was achieved in three steps by treating the myofibrils for 1 h each at 37° C. with the kits for alkaline phosphatase (Roche), protein phosphatase (PP)1 (New England Biolabs), and PP2A (Upstate Cell Signaling) [41]. After the treatment with PP2A, the pellet was dissolved in the buffer containing 7 M urea, 2 M thiourea, 4% CHAPS, 1% dithiothreitol, 1% destreaking agent, 1.5% ampholytes, and 0.01% bromophenol blue. The samples were stored at minus 80° C. until analysis.

Protein Assay

Protein concentration was determined using Bradford method by Bio-Rad Protein Assay kit and when needed, by amino acid analysis. All assays were performed in triplicate [42].

1D SDS-PAGE

Solubilized myofilament proteins were separated on a 4-12% NuPAGE Bis-Tris gel (1.0 mm, Invitrogen) and run using a MOPS-based running buffer.

In-Gel Digestion and Peptide Extraction

Upon completion of gel staining, individual bands were excised from the gel. In-gel digestion and peptide extraction was achieved using the improved protocol previously [43]. Briefly, cTnI bands were excised, cut into 1 mm$^3$ pieces, and washed 3 times with 50% acetonitrile/25 mM ammonium bicarbonate for 15 min with shaking. Gel pieces were incubated with 25 mM ammonium bicarbonate+10 mM dithiothreitol for 60 min at 55° C., washed with acetonitrile (ACN), then incubated with 20 mM ammonium bicarbonate+55 mM iodoacetamide (freshly made) for 30 minutes in the dark. The gel pieces were washed with acetonitrile, air dried, and rehydrated with 12.5 ng/µL, trypsin (Promega, sequencing grade, Madison, Wis.) in 25 mM ammonium bicarbonate, then incubated at 37° C. for 18 hr or overnight. The liquid was transferred to a clean tube. Peptides were extracted twice using 50% ACN+0.1 TFA % for 20 min at 25° C., followed by 20 min of shaking, 1 min of centrifugation, and combined two times of extraction with the liquid from the previous step.

Immunoblotting Analysis for Validation

Western blots were optimized for each antibody, by altering blocking conditions and concentrations of antibodies (primary and secondary). Chemiluminescence was used in its linear range. Primary antibodies were: for total TnI (81-7, a monoclonal antibody to TnI), phospho-TnI (Ser23/Ser24)(Cell Signaling Co.). Densitometrical analysis was done with a Progenesis image software (nonlinear dynamics), and the ratio of phospho-TnI to total TnI was calculated by Microsoft Excel software.

MRM Experiments

All assays were performed on a hybrid quadrupole/linear ion trap mass spectrometer (4000 QTrap, Applied Biosystems/MDS Sciex Foster City USA, Concord, Canada) using a nano-electrospray source. The spectrometer was capable of operating the final quadrupole as either a conventional transmission RF/DC resolving quadrupole mass filter or as an axial ejection linear ion trap mass spectrometer. The LINAC® collision cell minimizes the cross-talking effect in very fast MRM experiments (up to 5 ms per transition). For validation runs, the MRM traced trigger MS/MS spectrum acquisition on the two highest transitions. MS/MS spectra was acquired in the trap mode (enhanced product ion) with 100- or 300-ms fixed fill time with QO trapping enabled, Q1 resolution low (1.5 m/z half-maximum peak width), scan speed of 4000 amu/s, m/z range of 250-1500, and two scans summed. Quantitative analyses in MRM mode were performed with Q1 and Q3 operated in unit resolution (0.7 m/z half-maximum peak width) to maximize specificity. A series of transitions (precursor/fragment ion transitions) were measured sequentially, and the cycle (typically 1-2 sec) was looped throughout the entire time of the HPLC separation. The instrument parameters, e.g. declustering potential and collision energy were optimized automatically using automation software MRMPilot 1.0 (Applied Biosystems) in order to get maximal intensity of MRM transitions. For the scheduled MRM experiments a beta-version of the Analyst software (version1.52) (Applied Biosystems) were used.

Synthesized Internal Standards (SIS)

For absolute quantification, a series of SIS peptides (for cTnI, 48 peptides) were chemically synthesized (New England Peptide, MA). These peptides had been selected based on our initial in silico MRM design approach and using fully optimized experimental data. They were isotopically labeled by incorporating 15N/13C in one amino acid residue, typically Lys, Arg, Val, Phe, or Leu near the C-terminus (mass difference of 6-10 daltons). The incorporation of stable isotopes at the C-terminus ensured retention of the label in larger y-fragment ions of the reference peptide, thus facilitating precise quantification [44]. Non-degenerate fragments, i.e. ions with distinct masses, minimized cross-talking between the MRM transitions of the internal standard and the endogenous analyte. SIS peptides were spiked into tryptic digest of samples in selected experiments. The synthetic reference peptides were also useful for confirming the identity of the target peptide through perfect co-elution and by exhibiting identical fragmentation patterns. Six biological replicates were performed to obtain the statistical data.

Statistical Analysis

Quantification peak area was determined with Multiquant software (version 1.0 Applied Biosystems/MDS Sciex) after confirming for each peptide the coelution of all transitions. To ensure correct peak identification and quantification, peak detection was also inspected by the Multiquant software and visually for co-elution, similar shape, and for retention order. Peptides with unfavorable elution profiles (bad resolution) or interfering noise in the heavy or light transitions were excluded from further data analysis and from the transition table. Normalization was performed in four steps: 1) A ratio of peak area as light transition/heavy transition) was calculated to correct for spray efficiency and ionization differences between runs. 2) A mean of a particular transition over the six biological replicates was calculated. 3) To correct for systematic errors from uneven total protein starting material in the samples, we calculated all transition pairs for every peptide from every sample and used the resulting transition for normalizing the data. 4) The obtained response variables were log-transformed to fulfill the linear mixed-effects model assumption of residual normality and to stabilize their variance.

Example 1: MRM Assay

To date, various methods have been used to study protein phosphorylation. Methods such as Nuclear magnetic resonance (NMR) [6-7], Non-equilibrium isoelectric focusing (NEIEF) [8], radiolabeling with $^{32}$P [9], Pro-Q Diamond gel staining [10-13], phos-tags [14-15], phosphospecific antibodies [16] and some MS-based approaches [17] have all been used in different types of biological systems. However, none of these methods is routinely used to provide a highthroughput residue-specific detection and quantification of phosphorylation. The MRM assay is a MS-based method that allows for a simultaneous quantification of multiple phosphorylated peptides and their corresponding unphosphorylated forms (see FIG. 1 for example). One advantage of this technique is that more than one residue can be quantified in a single MS analysis. In fact, recent examples in the characterization of phosphorylation highlight the need for MRM assays robust enough to quantitatively profile more peptides and proteins in every LC run [18]. This targeted nano-LC/MS/MS-based approach reduces the potential problem with antibody nonspecificity, since MRM assays can offer high specificity and sensitivity due to the two-stage filtering both at the peptide (Q1, precursor ion) and fragment (Q3, daughter ion) level.

With MRM, samples are digested (most often with trypsin) and the resulting peptides (containing phosphorylated (P)) are analyzed using a triple quadrupole MS instrument, in our case, 4000 QTRAP LC/MS/MS. Specificity is obtained based on the peptide elution time from the online HPLC and the corresponding MS/MS data (Transitions: Q1/Q3 pairs). Three peptides and three transitions per peptide are commonly used for quantification of one protein. In our case, peptides that contain phosphorylation residues are specifically targeted. When more than one residue is monitored, a multiplex MRM assay can be developed. We have already done for all 12 phosphorylation residues on cTnI (see preliminary data) as well as the N- and C-terminus. With the Scheduled MRM™ Algorithm in Analyst® Software 1.5 (Applied Biosystem), up to 1000-2500 MRM transitions can be monitored in a single acquisition while maintaining the quantitative reproducibility that is essential for targeted protein quantification assays (FIG. 1). This approach can further provide absolute quantification of targeted proteins by incorporation of appropriate stable isotope-labeled peptides as internal standards. Because isotopes possess chemically and physically identical properties, the heavy labeled peptides will co-elute with light (native) peptides from the chromatographic column. Integration of the area beneath both peaks permits quantification of the proteins identified. Collectively, these characteristics make MRM ideally suited for the multiplexed quantification of proteins in complex samples and specifically target multiple potential phosphorylated residues [19-22]. However, despite the fact that sensitivity, selectivity, and dynamic range of the MRM assay, this technology has so far not been widely applied in cardiovascular disease. Described herein is an assay for phosphorylation analysis of cTnI in heart failure (FIG. 2).

Example 2: IDCM, ISHD and cTnI Phosphorylation

Myofilament dysfunction is implicated in cardiac disease such as ISHD (ischemic heart disease) and IDCM (idiopathic dilated cardiomyopathy). ISHD is a disease characterized by reduced blood supply to the heart muscle with resulting decreased function of partially or intermittently ischemic muscle or maladaptive dysfunction of remaining normally perfused regions, and is a common cause of heart failure. Patients with this condition may at one time have had a heart attack, angina, or unstable angina. Whereas IDCM is of undetermined but non-ischemic origin and is characterized by ventricular chamber enlargement and systolic dysfunction with an increased incidence of sudden death, thromboembolic risk, heart failure, and high overall mortality [23]. Alterations in myofilament protein phosphorylation are involved in the contractile dysfunction that occurs in failing animal model and human myocardium including cTnI [24-26], cTnT [27], myosin heavy and light chains [28]. Unfortunately, at present it is difficult to establish the relationship between different forms of pathology (heart failure: IDCM or ISHD) and specific residues of cTnI phosphorylation.

The myofilament consists of thin and thick filaments. The former is comprised of actin, tropomyosin (Tm), and troponin (Tn), while the latter myosin heavy chain associated with two light chains and myosin-binding protein C. Tn consists of three subunits, a calcium-binding subunit, TnC, the Tm-binding subunit, TnT, and the inhibitory subunit, TnI, which is responsible for inhibition of the actomyosin ATPase [29]. TnI is the switch from binding actin-Tm to TnC in the presence of $Ca^{2+}$ and thus ultimately regulates muscle contraction and relaxation. There are three isoforms of troponin I described for striated muscle. Cardiac TnI is larger than the other two skeletal isoforms due to the presence of an additional approximately 30-amino acid residue sequence at the N-terminal which contains the PKA phosphorylation sites. The phosphorylation of cTnI plays a pivotal role in the regulation of contractile activity of the heart.

There are six known phosphorylatable residues on cTnI (FIG. 3): serines at 23, 24, 42 and 44 (S23, S24, S42, and S44), a threonine at residues143 (T143), and at serine150 (S150) (using a numbering system including the initiating methionine in the mRNA encoding the molecule). The sites nearest the N-terminal (S23 and S24) are primarily phosphorylated by PKA, although PKG and PKC etc. can also phosphorylated them, whereas the other 3 sites (S42, S44 and T143) are primarily phosphorylated by PKC [30-31]. PKA dependent Ser23/24 phosphorylation has positive inotropic and lusitropic effects [32-34] while PKC-dependent Ser42/44 phosphorylation reduces systolic function and delays relaxation [35]. In this regard, PKA and PKC might also have opposing effects on cardiac efficiency. There may be other phosphorylation residues, including S150 [36] and S77/T78 [37] in human as well as other kinases that act on cTnI, including p21-activated kinase [36] and Mstl (mammalian sterile 20-like kinase 1) [38]. Interestingly, NetPhos 2.0, a phosphorylation prediction algorithm based on known amino acid consensus sequences of kinases, predicts 12 phosphosites out of total 23 potential cTnI sites. As shown in our preliminary data, we have now confirmed an additional 6 novel phosphorylation sites in cTnI (see preliminary data). Phosphorylation of cTnI plays an important role in the regulation of the contractile activity of the heart; therefore we intend to measure its phosphorylation status using the new MRM assay in heart failure diseases.

Example 3: New Phosphorylation Residues Found on Recombinant Human cTnI by the Treatment of PKA and PKC To obtain preliminary information on the peptide characteristics, both ionization and fragmentation, initial LC-MS/MS experiments were performed on recombinant human cTnI protein (rcTnI). Approximately 10 μg of recombinant rcTnI protein was treated in vitro with or without PKA and PKC, then reduced (100 mM DTT) and alkylated with iodoacetamide (200 mM) and digested with trypsin (0.1 μg). The resulting peptides were desalted by C18 Ziptip, dried and then suspended in 0.1% formic acid (FA) prior to MS analysis. Most commonly a full scan MS/MS spectrum in a LTQ Orbitrap is gathered. Once the precursor ion and fragmentation characteristics are noted, the precursor ion of interest and multiple fragment ions are chosen for MRM transitions and the sample is transferred to a triple quadrupole instrument. These transitions, based on the experimentally determined fragmentation pattern and CID parameters are further optimized on the QTrap LC/MS/MS. No phosphorylation event was found for the sample without treatment by kinases. However, we found several new phosphorylated residues with PKA and PKC treatment besides the known ones. These include for PKA, S5, Y26, T78, S166 and S199, and T51 residue for PKCα (FIG. 4).

Figure 5:
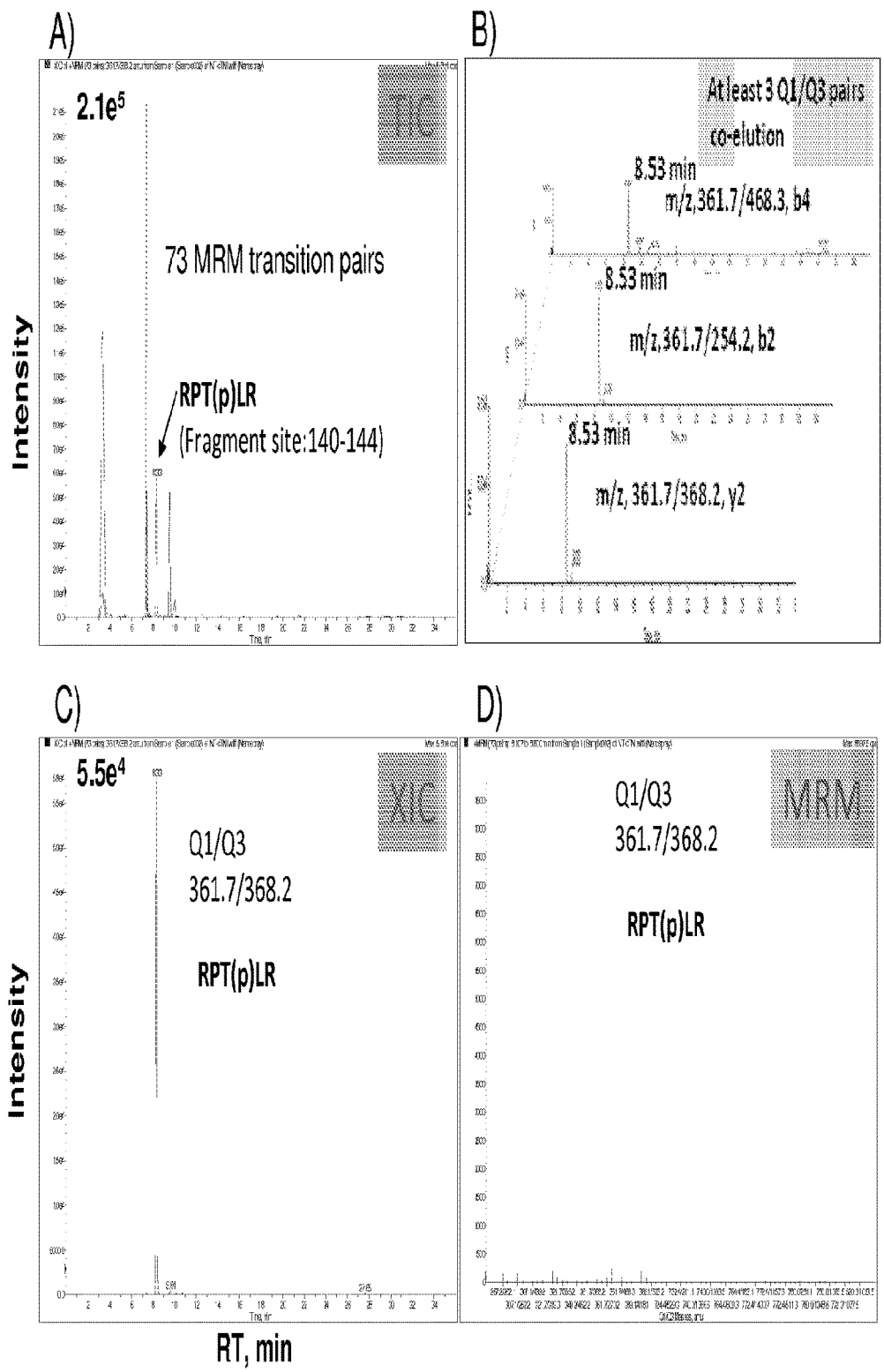
FIG. 5: Example of MRM assay for cTnI peptide RP(p)TLR.
Figure 6:
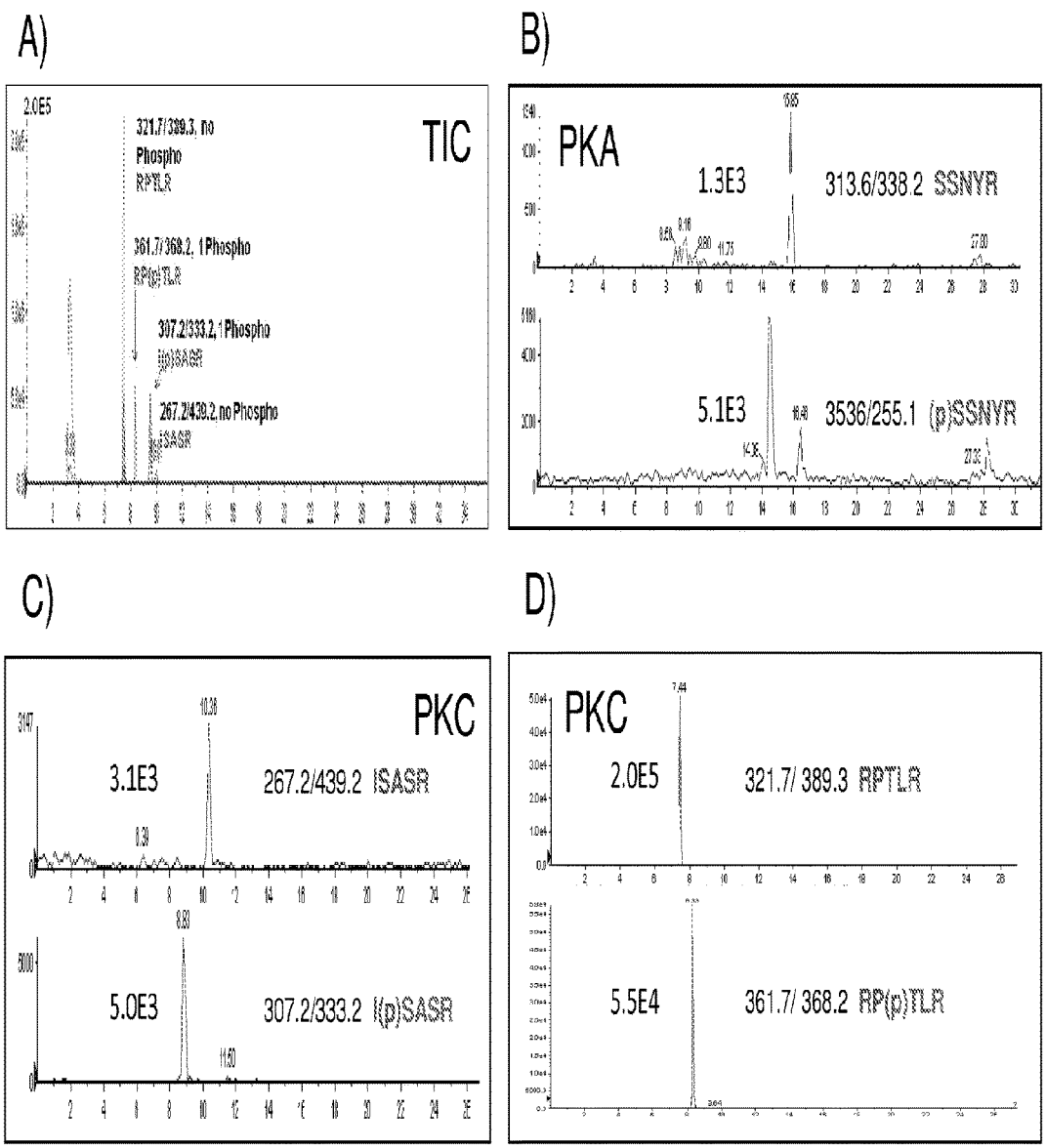
FIG. 6: MRM assay for multiply-phosphorylated sites of cTnI proteins.

First, we needed to develop a method that would allow us to ensure that cTnI could be solubilized and digested completely from human heart samples. This turned out to be more difficult than expected as cTnI is positively charged and insoluble under many conditions. Ultimately, human left ventricle (LV) myofibrils were isolated from a biopsy who was explanted in severe heart failure at time of transplantation, using 1% Triton X-100 in the presence of protease inhibitors (Roche complete mini protease inhibitor cocktail tablets), then proteins were extracted and resolved on a NuPAGE 4-12% Bis-Tris gel (Invitrogen). The resulting cTnI bands underwent in-gel digestion with trypsin for 18 h at 37° C., followed by peptide extraction and clean up using a ZipTip C18 (Millipore). Second, we needed to develop MRM assays for each phosphorylated and the corresponding non-phosphorylated residue in cTnI. In order to develop a MRM assay it is critical that the optimal peptides and MRM transitions are chosen identified and validated. We have developed a set of MRMs iteratively using three basic approaches: in silico design from software tool (MRMPilot), available LC-MS/MS proteomic survey data (PeptideAtlas), and comprehensive MRM testing of all of the candidate peptides of cTnI (QTrap+Orbitrap). In this approach, the protein sequence was digested in silico, likely y-ion and b-ion fragments are predicted, and theoretical MRMs were generated for all the peptides in an acceptable size window (250-1500 m/z). These MRMs were then used as a survey scan in a data-dependent experiment to detect specific peptide peaks, and each resulting MRM peak was examined by full scan MS/MS to obtain sequence verification of the hypothesized peptide. The identified peptides showing the best signal intensity and chromatographic peak shape were selected. A representative list of MRM transitions were used for the known PKC residue T143 in peptides PTLR and (R)PTLR (considering 1 missed cleavage) (Table 2). FIG. 5 shows an example in which 72 MRM transition pairs were used for identification of multiply phosphorylated peptides. Simultaneously, the analysis in a single run of nanoLC/MS/MS detected multiple phosphorylated peptides for PKC and PKA target residues, respectively (FIG. 6).

Example 4: Multiplex MRM Assay for the New Phosphorylated Residues Y26, 5166, T181 and 5199

Figure 7:
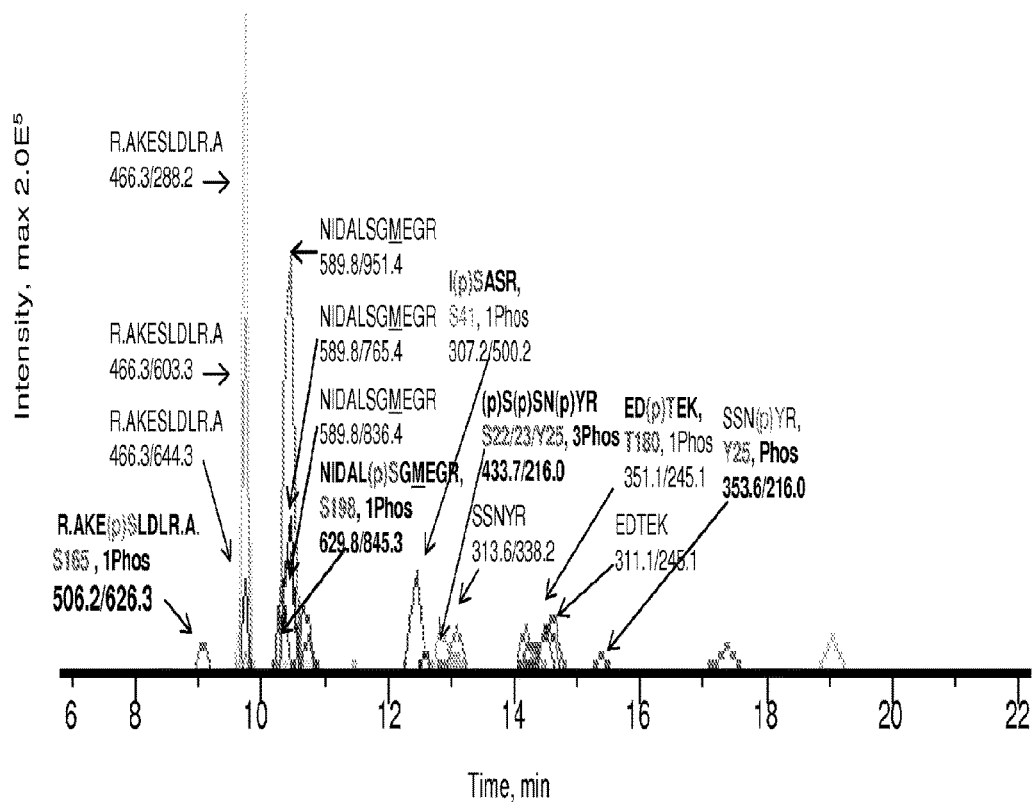
FIG. 7: Single MRM assay detect new multiple phosphorylated residues Y25, S165, T180 and S198 of cTnI proteins.

FIG. 7 showed that the multiplex MRM assay detected the new phosphorylated residues: Y26, 5166, T181 and S199 of cTnI, in the case of myofibrils isolated from two ISHD patients. For example, the new residue Y26 appeared at a monophosphorylated peptide: SSN(p)YR or as a very low tri-phosphorylated form of (p)S(p)SN(p)YR, although other diphosphorylated forms such as (p)SSN(p)YR or S(p)SN(p)YR could be detected depending on status of samples and phosphopeptides. Besides the novel sites, we detected the known PKC residue, S42 in I(p)SASR, at an intermediate peak intensity.

Figure 8:
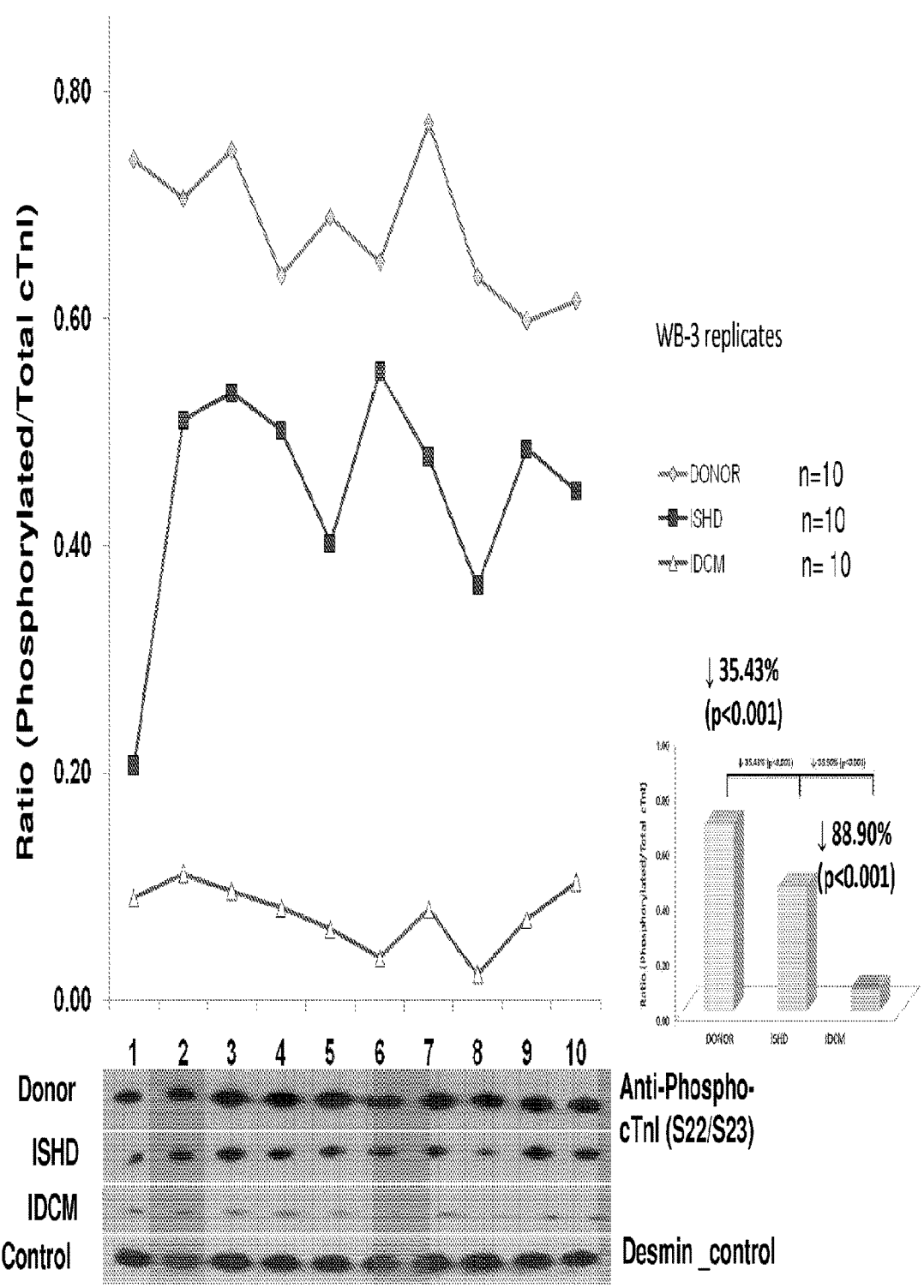
FIG. 8: Monophosphorylated cTnI at S22/23 decreased in ISHD and IDCM.

Example 5: Phosphorylation State of PKA Residues are Changed with HF: Confirmation by Western Blot To determine the level of cTnI phosphorylation in human myofibrillar extracts, western blots were performed using antibodies specific to the phosphorylated PKA residues S23 and S24. Myofilament proteins (100 ug), including cTnI, isolated from ISHD (n=10), IDCM (n=10) and non-failing donor (n=10) hearts (see table 2 for clinical information) were run by 1D NuPAGE 4-12% Bis-tris gel, transferred to the PVDF membranes. Western blots were then probed with several different available antibodies corresponding to the anti-cTnI antibody mAb 81-7 (amino acid residues 136-154) for a total cTnI protein), the anti-monophosphorylated cTnI S23/24 and anti-diphosphorylated cTnI (Serines 23+24) mAb 5E6, respectively. An anti-desmin antibody was used in triplicate as a loading control. Western blotting demonstrated that in human heart the phosphorylation of PKA target residue Ser23/24 was mainly present in the mono-phosphorylated form (FIG. 8), whereas there was only a small proportion in the amount of the diphosphorylated species (data not shown) and no diphosphorylation at Ser23/24 in ISHD and IDCM (data not shown). The important question that remains is whether the alterations are only involved in phosphorylation of the known PKA residues S23/24 or if other sites including the new ones are altered in heart failure. Due to the limitations in the availability of phosphosite-specific antibodies and traditional MS-based techniques, we have turned to MRM to answer this.

The cTnI endogenous phosphorylation status of some, but not all, of the phosphorylated residues (S5, Y26, T51, 5166, T181 and 5199) was significantly decreased in ISHD and IDCM as compared to the non-failing donor heart. The known PKA phosphorylation sites (S23/24) lie within the cardiac-specific N-terminal (residues 1-32) which interacts with the N-domain of cTnC. MRM assay showed that these sites have significantly decreased in HF when compared to the non-failing donor heart (the ratio of phosphorylated to unphosphorylated in Donor:ISHD:IDCM=0.136:0.039: 0.014; each type, n=10). This result was in compatible with the decreased trend of phosphorylation in HF by western blotting analysis using S23/24 site-specific phosphorylated antibodies (ISHD ↓35.43%, p<0.001 and IDCM ↓88.90%, p<0.001). Similar decline was found at the novel site Y26 (0.563:0.254:0.232) and S5 (0.36:0:0) due to their locations on the interaction region between cTnI and cTnC. However, phosphorylation ratio in HF was higher on the known PKC sites S42 (0.154:0.244:0.122) and T143 (2.326:3.36:4.044), and the unknown site S77 (0.575:1.147:0.887) as compared to donor heart. Relative higher ratio of cTnI phosphorylation in HF was also found on novel sites S166 (0.0107:0.0143: 0.0344), T181 (0.1428:0.2044:0.2207) and S199 (0.0047: 0.0142:0.0103).

Example 6: Identification of Unknown Protein Kinase Cα Phosphorylation Sites on Both Human Cardiac Troponin I and T Protein kinase C (PKC) isoforms have been shown to play an important role in the development of heart failure. Most research performed on PKCα has been done in rodents and direct evidence in human heart failure is limited. Our previous study showed a decrease in Ca2+-sensitivity in failing tissue upon PKCα treatment of cardiomyocytes via phosphorylation of cardiac troponin I (cTnI), cardiac troponin T (cTnT) and myosin binding protein C (cMyBP-C). This study aims to determine the targets of PKCα on cTnI and cTnT. Western immunoblotting revealed that PKCα is less abundant but more active in failing compared to donor tissue. PKCα treatment of donor and failing tissue was able to phosphorylate Thr-143, which is a known PKCα, site on cTnI, but endogenous phosphorylation levels were very low. LC-MS analysis of purified human recombinant cTn complex incubated with PKCα identified two novel phosphorylation sites, Ser-199 located on cTnI and Ser-189 on cTnT. Both sites are located in conserved regions on cTnI and cTnT. The PKA sites Ser23/24 on cTnI are phosphorylated by PKCα in purified human recombinant cTn complex, but there is no cross phosphorylation in donor and failing tissue. In conclusion, endogenous Thr-143 phosphorylation is low, which makes its involvement in heart failure unlikely. Exogenous PKCα, phosphorylation of Thr-143 and Ser-199 on cTnI and Ser-189 on cTnT could possibly explain the decrease in $Ca^{2+}$-sensitivity observed and further research on the site-specific effects is warranted.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

We claim:

1. A method of diagnosing and treating heart failure in a subject, comprising:
   (a) obtaining a biological sample from the subject;
   (b) measuring phosphorylation level at serine 5, tyrosine 26, serine 166, threonine 181 and/or serine 199 of a cardiac Troponin I protein or peptide in the biological sample by mass spectrometry, wherein the mass spectrometry is multiple reaction monitoring mass spectrometry;
   (c) diagnosing the subject with heart failure by comparing the measured phosphorylation level in the biological sample to a control level in a normal subject population; wherein a phosphorylation level decrease at serine 5, a phosphorylation level decrease at tyrosine 26, a phosphorylation level increase at serine 166, a phosphorylation level increase at threonine 181, and/or a phosphorylation level increase at serine 199, is indicative of heart failure in the subject; and
   (d) administering a treatment for heart failure to the subject.

2. A method of detecting cardiac Troponin I phosphorylation at serine 5, tyrosine 26, serine 166, threonine 181 and/or serine 199 comprising:
   (a) obtaining a test sample; and
   (b) analyzing the test sample by mass spectrometry to detect phosphorylated serine 5, tyrosine 26, serine 166, threonine 181 and/or serine 199 in the test sample, wherein the mass spectrometry is multiple reaction monitoring mass spectrometry.

3. The method of claim 1, further comprising detecting a level of a second marker indicative of heart failure.

4. The method of claim 3, wherein the second marker is cardiac specific isoforms of desmin, troponin T (TnT), CK-MB, myoglobin, or brain natriuretic peptide (BNP).

5. The method of claim 4, wherein the second marker is brain natriuretic peptide (BNP).

6. The method of claim 1, wherein the subject is a mammal.

7. The method of claim 1, wherein the subject is a human, dog, or horse.

8. The method of claim 1, wherein the subject is a human.

9. The method of claim 1, wherein the treatment for heart failure is selected from one or more of cardiac resynchronization therapy; heart valve repair or replacement; implantable cardioverter-defibrillator; heart pump; heart transplant; percutaneous coronary intervention; coronary bypass surgery; surgical correction of congenital heart defects; and administration of an angiotensin-converting enzyme inhibitor, angiotensin II receptor blocker, digoxin, beta blockers, diuretics, or aldosterone antagonist.

10. The method of claim 1, wherein the biological sample is blood, plasma, or serum.

11. The method of claim 1, wherein the biological sample is cardiac tissue, tissue homogenate, or tissue slice.

* * * * *